(12) United States Patent
Watabe et al.

(10) Patent No.: US 8,519,854 B2
(45) Date of Patent: Aug. 27, 2013

(54) FIRE ALARM SYSTEM

(75) Inventors: Yoshifumi Watabe, Tondabayashi (JP); Yoshiaki Honda, Souraku-gun (JP); Masanori Hayashi, Kadoma (JP); Yuji Takada, Kyoto (JP); Takayuki Nishikawa, Osaka (JP)

(73) Assignee: Panasonic Corporation, Osaka (JP)

( * ) Notice: Subject to any disclaimer, the term of this patent is extended or adjusted under 35 U.S.C. 154(b) by 596 days.

(21) Appl. No.: 12/682,300

(22) PCT Filed: Oct. 21, 2008

(86) PCT No.: PCT/JP2008/069002
§ 371 (c)(1),
(2), (4) Date: Apr. 9, 2010

(87) PCT Pub. No.: WO2009/054359
PCT Pub. Date: Apr. 30, 2009

(65) Prior Publication Data
US 2010/0259396 A1 Oct. 14, 2010

(30) Foreign Application Priority Data

| Oct. 26, 2007 | (JP) | 2007-279703 |
| Oct. 26, 2007 | (JP) | 2007-279705 |
| Oct. 26, 2007 | (JP) | 2007-279706 |
| Jun. 25, 2008 | (JP) | 2008-166265 |
| Oct. 9, 2008 | (JP) | 2008-263109 |

(51) Int. Cl.
*G08B 17/12* (2006.01)

(52) U.S. Cl.
USPC .......................................... 340/577

(58) Field of Classification Search
USPC .................. 73/801, 587; 340/577
See application file for complete search history.

(56) References Cited

U.S. PATENT DOCUMENTS 3,802,271 A * 4/1974 Bertelson ................ 73/865.5
6,405,603 B1   6/2002 Baumoel
(Continued)

FOREIGN PATENT DOCUMENTS

GB  2 299 668 A  10/1996
JP  61-180390 U  11/1986
(Continued)

OTHER PUBLICATIONS

International Search Report for the Application No. PCT/JP2008/069002 mailed Jan. 6, 2009.
Supplementary European Search Report for the Application No. EP 08 84 1498 dated Dec. 22, 2010.

*Primary Examiner* — Hezron E Williams
*Assistant Examiner* — Rodney T Frank
(74) *Attorney, Agent, or Firm* — McDermott Will & Emery LLP

(57) ABSTRACT

A fire alarm system, determining existence or nonexistence of a fire by using an ultrasound wave, comprises a sound wave generator and a sound wave detector to detect sound waves propagated through two propagation paths having different lengths each other. The system comprises a calculation means for calculating a pressure ratio between a first sound pressure, which is a sound pressure of a sound wave propagated through a first propagation path, and a second sound pressure, which is a sound pressure of a sound wave propagated through a second propagation path, and a smoke density estimator. The smoke density estimator calculates a change ratio between the pressure ratio calculated by the calculation means and a predetermined standard pressure ratio, and determines a smoke density from the change ratio based on a predetermined relational expression describing the relation between the change ratio and the smoke density, and determines existence of a fire when the smoke density exceeds a predetermined threshold.

12 Claims, 13 Drawing Sheets

(56) References Cited

U.S. PATENT DOCUMENTS

| | | | |
|---|---|---|---|
| 7,493,816 B1* | 2/2009 | Petrovic et al. | 73/570.5 |
| 2002/0080040 A1* | 6/2002 | Schneider et al. | 340/628 |
| 2006/0052963 A1 | 3/2006 | Shkarlet | |
| 2009/0184830 A1* | 7/2009 | Watabe et al. | 340/628 |

FOREIGN PATENT DOCUMENTS

| | | |
|---|---|---|
| JP | 10-339672 A | 12/1998 |
| JP | 2005-258747 A | 9/2005 |

* cited by examiner

FIRE ALARM SYSTEM

TECHNICAL FIELD

The invention relates generally to fire alarm systems, and more particularly to a fire alarm system that estimates a smoke density in a monitoring space by using a sound wave and determines existence or nonexistence of a fire based on this smoke density.

BACKGROUND ART

Japanese Patent Application Laid-Open No. 2005-258747 discloses a fire alarm system using a sound wave. This system estimates a density of smoke existing in a monitoring space and temperature of the monitoring space, and determines existence or nonexistence of a fire, based on a fluctuation of a sound pressure at a time when a sound wave sent from a sound source is received through the monitoring space and a fluctuation of a time until the sound wave is received.

However, due to a change with the passage of time of a sensor for receiving the sound wave and a characteristic change depending on temperature and humidity, the received sound pressure undergoes a lot of changes. Thus, it becomes impossible to distinguish this change of the sound pressure and an attenuation of the sound pressure depending on a smoke existing in the monitoring space, and the system, which estimates the smoke density based on the sound pressure of the received sound wave, has a problem that it is impossible to detect the attenuation accurately.

DISCLOSURE OF THE INVENTION

It is an object of the present invention to detect a smoke density in a monitoring space accurately and to transmit a reliable fire alarm, even if characteristics of a sound source and an element for receiving a sound wave changes.

A fire alarm system of the present invention comprises a sound wave generator sending a sound wave, a sound wave detector being located so as to sandwich in a monitoring space between itself and the generator and detecting the sound wave sent from the generator through the monitoring space, a controller being configured to control the generator and the sound wave detector, and a processing circuit being configured to process an output detected by the sound wave detector. The processing circuit comprises a sound pressure detector for detecting a sound pressure from the output, a smoke density estimator for estimating a density of smoke existing in the monitoring space and a fire alarm device being configured to transmit fire alarm when the smoke density estimated by the smoke density estimator exceeds a predetermined threshold. The generator and the sound wave detector are located in the monitoring space so as to form a first and second propagation paths for propagating the sound wave from the generator to the sound wave detector. And lengths of the first and second propagation paths differ from each other. The processing circuit comprises a calculation means for calculating a pressure ratio between a first sound pressure being a sound pressure of a sound wave propagated through the first propagation path and a second sound pressure being a sound pressure of a sound wave propagated through the second propagation path. The smoke density estimator is configured to calculate a change ratio between the pressure ratio and a predetermined average pressure ratio, and to determine the smoke density from the change ratio based on a predetermined relational expression describing the change ratio in relation to the smoke density.

Even if the sound pressure of the sound wave sent from a sound wave-generating element constituting the generator changes and a sensitivity of a wave-receiving element constituting the sound wave detector changes due to a change with the passage of time of the sound wave-generating element and the wave-receiving element, these changes influence a first and second sound waves equally. So these changes don't influence the pressure ratio calculated by the calculation means. Therefore, the fire alarm system can calculate a change ratio between the pressure ratio calculated by the calculation means and a predetermined average pressure ratio, and can estimate the smoke density through the smoke density estimator based on a predetermined relational expression describing the change ratio in relation to the smoke density. As a result, non-transmitting a fire alarm (false alarm) and lost alarm (this is, a signal is too small to transmit a fire alarm) can be prevented, and a reliable fire alarm system can be achieved.

In the fire alarm system of the present invention, it's preferred that a function determining a type of floating particles existing in the monitoring space and accurately estimating a density corresponding to the type are added. In this case, the generator is configured to send a single sound wave having a first and second frequency components differing from each other, and the processing circuit comprises a separation means for separating the first and second frequency components. The sound pressure detector is configured to detect sound pressures about the first and second frequency components, respectively. The processing circuit comprises a particle estimator for estimating a type of floating particles based on the pressure ratio outputted from the calculation means. The particle estimator is configured to calculate a relative change ratio between a first change ratio calculated in reference to the first frequency component and a second change ratio calculated in reference to the second frequency component. On the other hand, the processing circuit comprises a memory for storing a relative change ratio table having different relative change ratios corresponding to different types of floating particles and a density table having different smoke densities corresponding to different first change ratios. The particle estimator is configured to estimate a type of floating particles, corresponding to the relative change ratio, in the relative change ratio table. The smoke density estimator is configured to estimate a smoke density, corresponding to the first change ratio, in the density table if the type of floating particles is smoke.

In this configuration, by using a single sound wave having a plurality of frequency components, a type of floating particles can be determined and a smoke density can accurately be estimated if the type of floating particles is smoke, so cost can be decreased compared with a configuration to send a plurality of sound waves from the generator. In addition, by extracting intensities (sound pressures) of the plurality of frequency components from the single sound wave sent from the generator at one time, this configuration isn't influenced by dispersion generated between sound pressures when each of sound waves is sent, and estimation accuracy of the type of floating particles and the density can be improved.

It's preferred that the generator is configured to generate a sound wave of a single pulse. In the sound wave of a single pulse, there is few difference between intensities of frequency components, and the sound wave has power spectrum shaped so that power is distributed over a relatively wide range of frequency, so in a means for extracting frequency components there is few difference between intensities, and intensities of a relatively wide range of frequency components can be extracted, and the type of floating particles can be estimated accurately.

It's preferred that the separation means comprises frequency filters letting sound waves of the first and second frequency components pass through, respectively, and the calculation means is configured to calculate the pressure ratio about the sound waves of the first and second frequency components passing through the frequency filters. In this case, for example, lord of signal processing can be decreased compared with a configuration to perform fast Fourier transformation about time-series data outputted from a wave-receiving element and to extract intensity of each of frequency components.

In the fire alarm system of the present invention, it's preferred that the generator comprises a single wave-generating element and the sound wave detector comprises a single wave-receiving element. In a related matter, it's preferred that a first reflector and a second reflector are used and the first and second propagation paths are formed between the first reflector located at the side of the wave-generating element and the second reflector located at the side of wave-receiving element. In this case, the first propagation path is set as the shortest straight path between the wave-generating and wave-receiving elements, and the second propagation path is set as a reflex path through which a sound wave sent from the wave-generating element is reflected by the second reflector and the first reflector and is leaded to the wave-receiving element.

In this configuration, the sound wave is reflected the first reflector and the second reflector while using the single wave-generating element and the single wave-receiving element, so it becomes possible to propagate the sound wave to the single wave-receiving element through propagation paths, having different lengths each other, corresponding to reflection times, then the pressure ratio can be calculated. In addition, because it's becomes possible to calculate the pressure ratio about the sound wave sent from the generator at one time, the calculated pressure ratio isn't influenced by dispersion of sound pressures depending on a timing of driving the generator and an accurate fire determination can be achieved. And by using the reflectors, the propagation paths having different lengths each other can be achieved in the inside of the minimum size and a fire sensor can be downsized.

In the fire alarm system of the present invention, it's preferred that a function correcting a change of the pressure ratio depending on an environment change of air temperature, humidity and atmospheric pressure etc. is added. Consequently, the processing circuit comprises a parameter measuring means for measuring at least one parameter of air temperature, humidity and atmospheric pressure, and an environment change correcting means for correcting a change of the pressure ratio depending on an environment change based on the parameter, and by correcting the pressure ratio based on a correction relational expression expressed with these one or more parameters, influence of the environment change can be canceled and an estimation accuracy of the density can be improved more.

In a related matter, the environment change correcting means is configured to correct the change of the pressure ratio depending on the environment change, based on the sound speed showing air temperature and humidity which are one of the above mentioned parameters. In this case, the processing circuit is configured to measure the sound speed by dividing a length of the first propagation path by a time difference between a timing of detecting the first sound pressure and a timing of driving the generator. By using this system, the sound speed can be measured without addition of a new element. It becomes possible to calculate humidity based on air temperature obtained by a temperature measuring means and the sound speed, when for example atmospheric pressure is constant. It becomes possible to correct the change of the pressure ratio by using air temperature and humidity, which make relatively large influence on the environment change, for the parameters.

In the fire alarm system of the present invention, it's preferred that a function correcting a change of the pressure ratio depending on a change with the passage of time of reflective performance in the first and second reflectors is added. Consequently, the fire alarm system is configured to detect sound pressures in a first propagation path, a second propagation path and a third propagation path, which are formed between the first and second reflectors, respectively. The number of reflection times of a sound wave propagated through the second propagation path to the wave-receiving element is more than the number of reflection times of a sound wave propagated through the first propagation path to the wave-receiving element. And the number of reflection times of the sound wave propagated through the second propagation path is less than the number of reflection times of a sound wave propagated through a third propagation path to the wave-receiving element. The processing circuit comprises a reflection change calculating means for calculating a relative change ratio for a default value about reflective performance in the reflectors, and a reflection change correcting means for correcting the pressure ratio based on the relative change ratio. The reflection change calculating means is configured to calculate the relative change ratio, based on a pressure ratio among the first sound pressure obtained by receiving the sound wave propagated through the first propagation path, the second sound pressure obtained by receiving the sound wave propagated through the second propagation path and a third sound pressure obtained by receiving the sound wave propagated through the third propagation path, which are different from each other in the number of reflection times.

In this configuration, sound pressures of a first, second and third sound waves, which are propagated through propagation paths having different lengths each other, are measured. Compared a ratio between the first and second sound pressures with a ratio between the first and third sound pressures, the numbers of reflection times are different from each other and influence degree is different when a reflection ratio of the reflector changes. Therefore, it becomes possible to calculate a relative change for a default value (a value included in the pressure ratio) and it's becomes possible to estimate the smoke density accurately by correcting the ratio between the first and second sound pressures based on this reflection change.

In the present invention, other system, which achieves a function for estimating a type of floating particles existing in the monitoring space and determining a density corresponding to the type accurately, is disclosed. In this system, the generator is configured to send sound waves having a first and second frequencies differing from each other, respectively. The processing circuit comprises a particle estimator for estimating a type of floating particles based on the pressure ratio outputted from the calculation means. The particle estimator is configured to calculate a relative change ratio between a first change ratio and a second change ratio which are calculated in reference to the sound waves of the first and second frequencies, respectively. In this system, the processing circuit also comprises a memory for storing a relative change ratio table having different relative change ratios corresponding to different types of floating particles, and a density table having different densities of smoke corresponding to different first change ratios. The particle estimator is configured to estimate a type of floating particles, corresponding to the relative change ratio, in the relative change ratio table. The smoke density estimator is configured to estimate a smoke density, corresponding to the first change ratio, in the density table if the type of floating particles is smoke.

It's preferred that the generator in the above mentioned system comprises a single sound source. The controller is configured to drive the sound source so as to send the sound waves, having the first and second frequencies differing from each other, from the sound source sequentially. In this case, the calculation means synchronizes the controller and is configured to calculate pressure ratios, in relation to the sound waves having the first and second frequencies, from the sound wave detector, respectively. Thus, by using the single sound source, a configuration of an outputting section of a sound wave becomes simple and allows downsizing. In the fire alarm system of the present invention, it's preferred that each of the first and second reflectors has a reflection surface formed into concave with respect to the wave-generating and wave-receiving elements located so as to face the first and second reflectors, respectively. And it's preferred that the reflectors is configured to let a sound wave collect in the wave-generating or wave-receiving elements, and the wave-generating and wave-receiving elements are located at exposed parts of the reflection surfaces of the first and second reflectors, respectively. In this configuration, it is hard to diffuse a sound wave even if the sound wave repeats the reflection in reflection surfaces, so a decrease of a sound pressure depending on diffusion of a sound wave between the generator and the wave-receiving element can be prevented. Therefore, a sound pressure of a sound wave received in the wave-receiving element can be maintained highly when there is no smoke particle in the monitoring space. The amount of change outputted from the wave-receiving element to the amount of change of smoke density becomes relatively large, and there is an advantage that the signal to noise ratio is improved.

It's preferred that in the present invention the first and second reflectors are located between a pair of nonproliferation plates, and at both ends in height directions of the first and second reflectors, the monitoring space is occluded with the nonproliferation plates, and the wave-generating element is located at an intermediate part in a length direction of the first reflector, and at the intermediate part of the first reflector, a generation face of the wave-generating element is configured to cover the whole of a height direction of the first reflector. It can prevent that a sound wave propagated between a first and second reflection surfaces escapes from propagation paths formed between these reflectors, and a sound pressure decreases. The signal to noise ratio can be maintained highly, and a pressure ratio determining the smoke density accurately can be obtained.

BRIEF DESCRIPTION OF THE DRAWINGS

Preferred embodiments of the invention will now be described in further details. Other features and advantages of the present invention will become better understood with regard to the following detailed description and accompanying drawings where.

BEST MODE FOR CARRYING OUT THE INVENTION

A fire alarm system of the present invention measures a density of smoke as floating particles existing in a monitoring space by using an ultrasound wave, and transmits a fire alarm when the smoke density exceeds a predetermined threshold. The fire alarm system is configured to estimate the smoke density based on a pressure ratio between sound pressures of sound waves propagated through propagation paths having different lengths each other, respectively. In embodiments described below, a case where a single fire sensor attached to the indoor ceiling of a building achieves the fire alarm system of the present invention is explained. But the present invention isn't limited to this case, also includes a case where a fire sensor and a master station communicating with the fire sensor through wireless or wired achieve the fire alarm system.

First Embodiment

Figure 1:
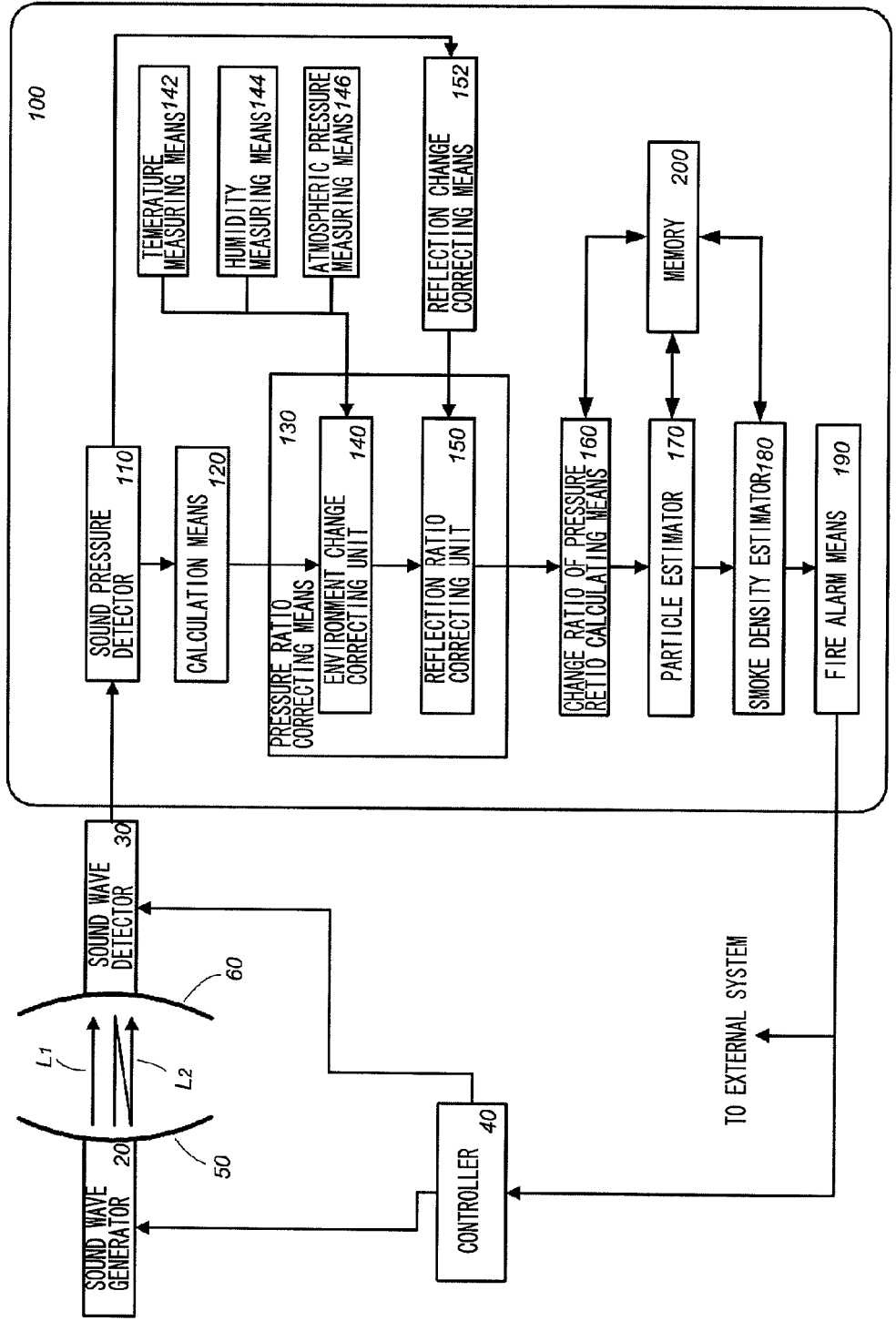
FIG. 1 is a schematic showing a fire alarm system according to a first embodiment of the present invention.

A fire alarm system according to a first embodiment of the present invention, as shown in FIG. 1, comprises a sound wave generator 20 sending an ultrasound wave, a sound wave detector 30, a controller 40 controlling the generator 20 and the sound wave detector 30, and a processing circuit 100. The processing circuit 100 processes an output detected by the sound wave detector 30 and estimates a smoke density and transmits a fire alarm. Then, a fire sensor attached to the indoor of a building is equipped with these generator, detector, controller and circuit. The generator and the sound wave detector comprise a single wave-generating element 20 and a single wave-receiving element 30, respectively. A detection unit 10 is constituted by combining both elements 20, 30 with a first and second reflectors 50, 60. The first and second reflectors 50, 60 are located so as to separate a predetermined distance each other, and a monitoring space is set between the first and second reflectors 50, 60. The wave-generating element 20 is located at an intermediate part in a length direction of the first reflector 50, and the wave-receiving element 30 is located at an intermediate part in a length direction of the second reflector 60. Therefore, propagation paths, for propagating sound waves, which have different lengths each other are set between both elements 20, 30. In other words, a first propagation path L1 through which a sound wave sent from the wave-generating element 20 is directly propagated to the wave-receiving element 30, and a second propagation path L2 through which a sound wave sent from the wave-generating element 20 propagated to the wave-receiving element 30 after being reflected by the second reflector 60 and the first reflector 50 are obtained. The controller 40 detects a sound wave propagated through the first propagation path and a sound wave propagated through the second propagation path, by being synchronized with an output timing of a sound wave sent from the wave-generating element 20 and driving the wave-receiving element 30.

The controller 40 comprises a circuit controlling the wave-generating element 20 so as to send an ultrasound wave intermittently, and a circuit controlling so as to be synchronized with a timing to which a sound wave reaches the wave-receiving element 30 through the first and second propagation paths and to send an output to the processing circuit 100.

Figure 2:
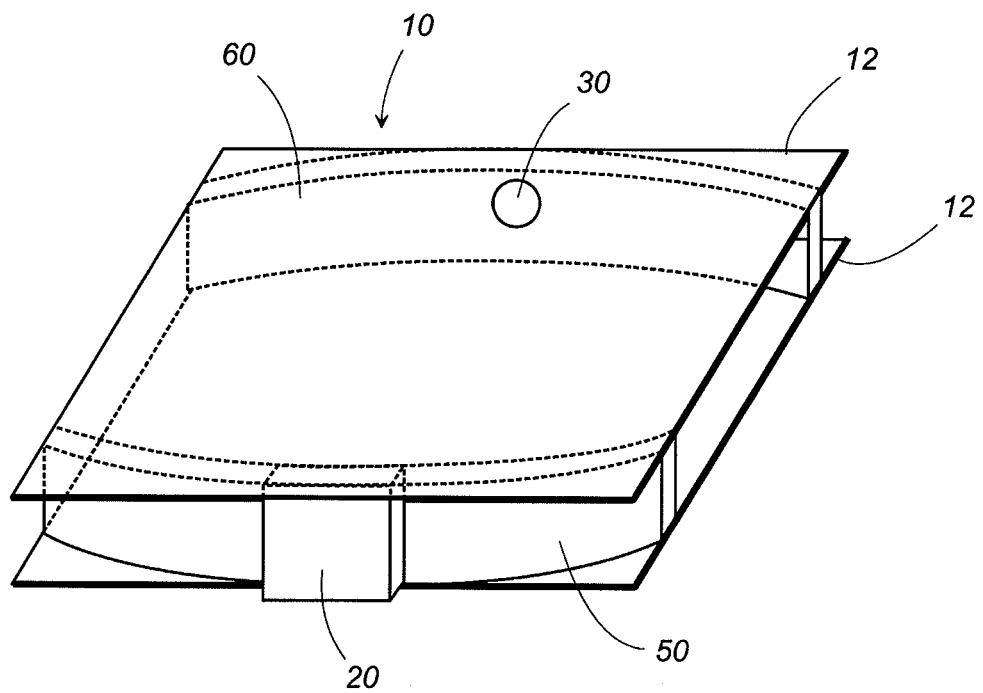
FIG. 2 is a perspective view showing a detection unit used in a fire alarm system according to a first embodiment of the present invention.

The detection unit 10, as shown in FIG. 2, comprises a pair of nonproliferation plates 12, 12 and the first and second reflectors 50, 60 are located between the nonproliferation plates. A space surrounded by these components is set as a monitoring space. Each of the first and second reflectors 50, 60 has a uniform height, and each of reflection surfaces facing each other is formed into concave. The first and second reflectors 50, 60 reflect a sound wave toward the sides of the wave-receiving element 30 and the wave-generating element 20, respectively. The wave-generating element 20 is located at the intermediate part of the first reflector 50 so that own height covers the whole of a height direction of the first reflector 50. A sound wave diffused along a height direction of the detection unit 10 is intercepted with the nonproliferation plates 12, 12. The detection unit 10 opens in the both ends of a length direction of each of the reflectors, and external atmosphere is introduced in the monitoring space through these openings.

The processing circuit 100 is configured to estimate a density of smoke existing in the monitoring space, based on an output detected by the wave-receiving element 30 and to determine existence or nonexistence of a fire. Before explanation of the concrete configuration of the processing circuit 100, the basic principle of the present invention, which estimates a smoke density based on a pressure ratio between different sound pressures detected in the wave-receiving element through propagation paths having different lengths, is explained referring to FIGS. 3A, 3B and 3C.

Figure 3A:
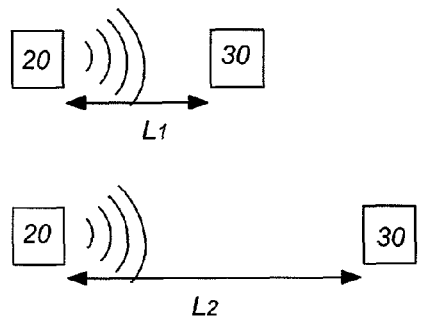
FIGS. 3A, 3B, and 3C are schematics showing a base principle of the present invention.
Figure 3A:
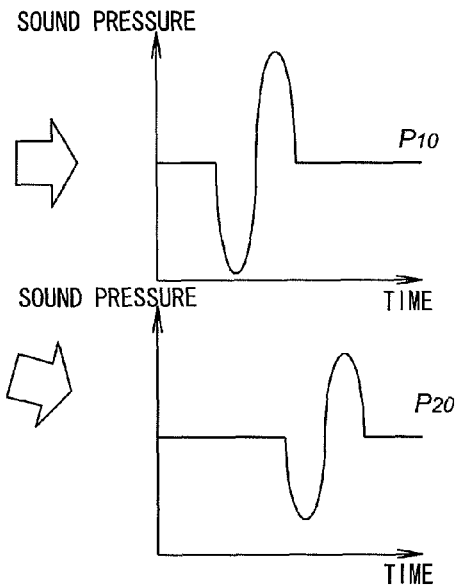

Sound waves, as shown in FIG. 3A, which are propagated to the wave-receiving element 30 through propagation paths having different lengths $L_1$, $L_2$, respectively, shows different sound pressures $P_{10}$, $P_{20}$, if atmosphere environment (for example, air temperature, humidity and atmospheric pressure) where the fire sensor is used is in the usual state and the wave-generating element and the wave-receiving element are in default condition in which a change with the passage of time isn't produced and floating particles (smoke particles are included) don't come in the monitoring space. Because a sound pressure decreases in proportion to a length of a propagation path, the sound pressure $P_{20}$ of an ultrasound wave propagated through a propagation path having length $L_2$ becomes low compared with the sound pressure $P_{10}$ of an ultrasound wave propagated through a propagation path having length $L_1$ ($<L_2$), and a default pressure ratio $R_0$ becomes ($R_0 = P_{20}/P_{10}$).

Figure 3B:
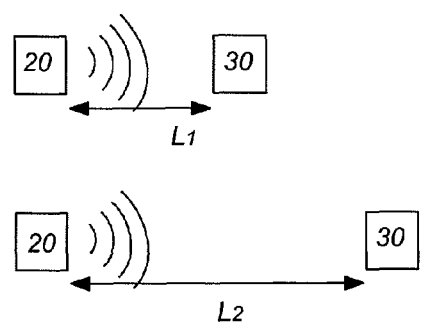
Figure 3B:
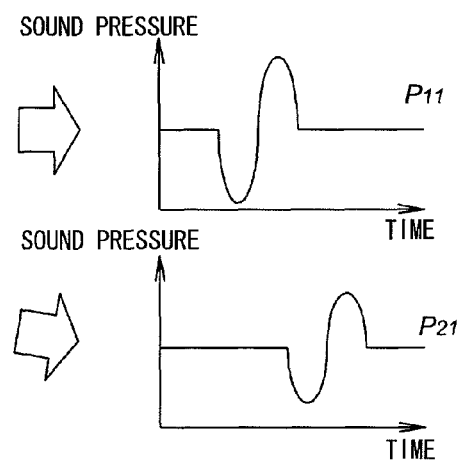

A sound pressure $P_{11}$ of an ultrasound wave propagated through a propagation path having length $L_1$ and a sound pressure $P_{21}$ of an ultrasound wave propagated through a propagation path having length $L_2$, as shown in FIG. 3B, become low compared with the sound pressures ($P_{10}$, $P_{20}$) shown in FIG. 3A, respectively, but a pressure ratio $R_1$ (that is, $P_{21}/P_{11}$) becomes equal to the default pressure ratio $R_0$, if a characteristic change is produced due to a change with the passage of time of the wave-generating element 20 and the wave-receiving element 30 and floating particles (smoke particles are included) aren't existing in the monitoring space. In other words, the characteristic change, due to a change with the passage of time of the wave-generating element 20 and the wave-receiving element 30, doesn't influence the pressure ratio $R_1$.

Figure 3C:
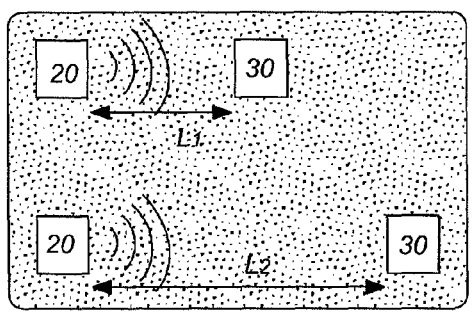
Figure 3C:
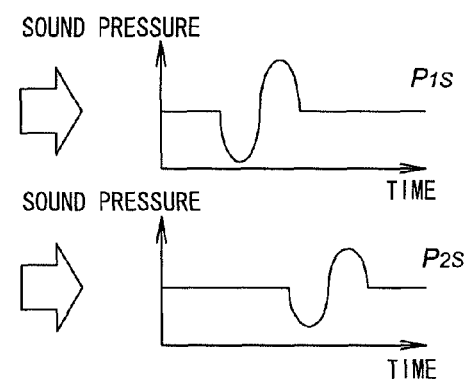

On the other hand, not only a sound pressure $P_{1s}$ of an ultrasound wave propagated through a propagation path having length $L_1$ and a sound pressure $P_{2s}$ of an ultrasound wave propagated through a propagation path having length $L_2$, as shown in FIG. 3C, become low compared with the values shown in FIGS. 3A and 3B, but also a pressure ratio ($R_s = P_{2s}/P_{1s}$) changes, if smoke particles (or other floating particles) come in the monitoring space between the wave-generating element 20 and the wave-receiving element 30. In other words, because a loss of a sound pressure detected in the wave-receiving element 30 depends on both a propagation distance of an ultrasound wave and a smoke density in the monitoring space if smoke particles come in the monitoring space, the pressure ratio $R_s$ changes from the default pressure ratio $R_0$ corresponding to a difference ($L_2-L_1$) of the lengths $L_1$, $L_2$ and a smoke density in the monitoring space. The amount of change of this pressure ratio shows the smoke density in the monitoring sp ace.

Explaining concretely, if C[%/m] is the smoke density by the above mentioned light extinction system in the monitoring space and α is a loss ratio of an ultrasound wave of per 1 [m] to the smoke density 1 [%/m], the sound pressure $P_{1s}$ of an ultrasound wave propagated through the length $L_1$ can be expressed with $P_{1s} \approx P_{10}(1-\alpha \cdot CL_1)$, and the sound pressure $P_{2s}$ of an ultrasound wave propagated through the length $L_2$ can be expressed with $P_{2s} \approx P_{20}(1-\alpha \cdot CL_2)$, and the amount of change $(R_0-R_s)$ from the default pressure ratio $R_0$ to the pressure ratio $R_s$ $(=P_{2s}/P_{1s})$ can be expressed with the following formula.

$$R_0-R_s=R_0\cdot\alpha\cdot C(L_2-L_1)/(1-\alpha\cdot L_1) \qquad 5$$

At this time, if a $\alpha\cdot L_1$ is sufficiently smaller than 1, it becomes $R_0-R_s=R_0\cdot\alpha\cdot C(L_2-L_1)$. Then, the amount of change $(R_0-R_s)$ from the default pressure ratio $R_0$ to the pressure ratio $R_s$ is expressed with a formula proportional to the difference $(L_2-L_1)$ of the lengths and the smoke density C in the monitoring space. Therefore, if a, $L_1$ and $L_2$ are known, the smoke density C[%/m] in the monitoring space can be estimated based on the amount of change $(R_0-R_s)$ from the default pressure ratio $R_0$ to the pressure ratio $R_s$. Or, the smoke density can be estimated based on a change value $(R_0-R_s)/R_0$ dividing the amount of change from the default pressure ratio $R_0$ to the pressure ratio $R_s$ by the default pressure ratio $R_0$. In other words, in the present invention, such the amount of change $(R_0-R_s)$ and the change value $(R_0-R_s)/R_0$ are used as a change ratio, and the smoke density is estimated based on this change ratio. The default pressure ratio $R_0$ which is a characteristic value for the system is stored in a memory 200 of the processing circuit 100.

Hereinafter, the processing circuit 100 is explained in detail. As shown in FIG. 1, the processing circuit 100 comprises a sound pressure detector 110 for detecting a sound pressure based on an output detected by the wave-receiving element 30, a calculation means 120 for calculating a ratio between a first sound pressure of a sound wave propagated through the first propagation path (length $L_1$) and a second sound pressure of a sound wave propagated through the second propagation path (length $L_2$), a pressure ratio correcting means 130 for correction a pressure ratio produced with a change of the air of ambient environment and a change of the reflective performance of the first and second reflectors 50, 60, a change ratio of pressure ratio calculating means 160 for calculating a change from the default pressure ratio $R_0$ to the calculated pressure ratio $R_s$, a particle estimator 170 for estimating a type of floating particles based on the change ratio of pressure ratio, a smoke density estimator 180 for estimating a density of estimated particles, and a fire alarm means 190 for determining existence of a fire and generating a fire alarm signal if a estimated smoke density exceeds a predetermined threshold. This fire alarm signal is sent to the controller 40. Then, the controller 40 generates a drive signal which makes the wave-generating element 20 generate an alarm sound having a frequency of zone of audibility when receiving this fire alarm signal. Therefore, a beep sound can be generated without attaching a speaker separately. This fire alarm signal is also sent to an external alarm system and then warning is made at places other than a fire spot.

The pressure ratio correcting means 130 is mentioned later. Hereinafter, a processing for determining existence of a fire based on a corrected pressure ratio is explained. The change ratio of pressure ratio calculating means 160 calculates a change ratio $(V=(R_0-R_s)/R_0)$ based on the default pressure ratio $R_0$ stored in the memory 200 and a present pressure ratio $R_s$, and then outputs this change ratio to the particle estimator 170. For example, if each of the first and second reflectors 50, 60 is formed into concave which is 150 mm in radiuses and an interval between the wave-generating element 20 and the wave-receiving element 30 is 150 mm, the default pressure ratio $R_0$ changes with frequency of an ultrasound wave to be used and is set to a value as shown in Table 1.

TABLE 1

DEFAULT PRESSURE RATIO TABLE

| FREQUENCY (kHz) | DEFAULT PRESSURE RATIO ($R_0$) |
|---|---|
| 20 | 0.36 |
| 54 | 0.41 |
| 69 | 0.45 |
| 82 | 0.48 |

Figure 4:
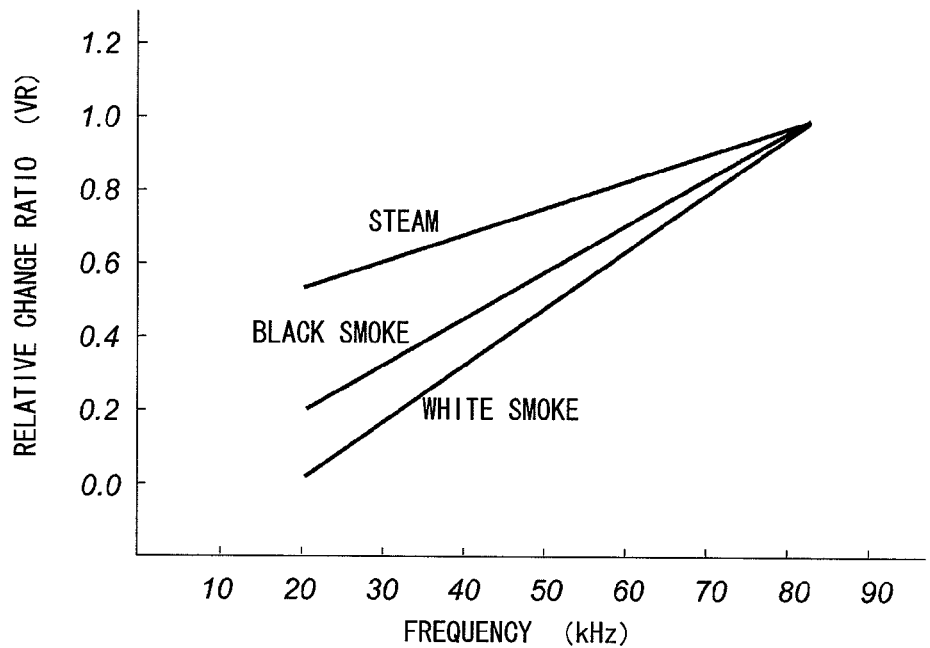
FIG. 4 is a graph explaining a method for estimating a type of particles of a fire alarm system according to a first embodiment of the present invention.

In the memory 200, data showing relative change ratios (VR) corresponding to several types of floating particles (for example, steam, black smoke and white smoke), respectively, is also stored. The relative change ratios (VR) is a ratio between a standard change ratio $V_{82}$ calculated by using an ultrasound wave of a standard frequency (for example, 82 kHz) and a change ratio $V_{20}$ calculated by using an ultrasound wave of a predetermined frequency, for example, 20 kHz or 54 kHz, under environment where the density of each of floating particles is 1%/m. Such data, as shown in the following Table 2, is prospectively calculated about several useful frequencies and can be expressed with a graph shown in FIG. 4.

TABLE 2

RELATIVE CHANGE RATIO TABLE

| FREQUENCY (kHz) | TYPES OF FLOATING PARTICLES | RELATIVE CHANGE RATIO VR (RATIO BETWEEN A STANDARD CHANGE RATIO AND A CHANGE RATIO) |
|---|---|---|
| 20 | STEAM | 0.53 |
|  | BLACK SMOKE | 0.18 |
|  | WHITE SMOKE | 0.04 |
| 54 | STEAM | 0.76 |
|  | BLACK SMOKE | 0.62 |
|  | WHITE SMOKE | 0.52 |

When the particle estimator 170 estimates a type of floating particles, it is necessary to calculate the change ratio $V_{82}$ when using an ultrasound wave of a standard frequency, and the change ratio $V_{20}$ when using an ultrasound wave of a specific frequency (for example, 20 kHz) differing from the standard frequency, respectively. Consequently, the wave-generating element 20 is configured to send sound waves having frequencies differing from each other by controlling of the controller sequentially.

The particles estimator 170 calculates a relative change ratio $(VR=V_{20}/V_{82})$, which is a ratio between an actual change ratio measured by using an ultrasound wave of a standard frequency and a change ratio calculated by using an ultrasound wave of a specific frequency differing from the standard frequency. Then, the particles estimator 170 refers to a relative change ratio table, and estimates a type of a measured particles to a type of which floating particles shows the value nearest to an actual calculated relative change ratio VR in the table, in the specific frequency (here, 20 kHz).

In addition, as shown in the following Table 3, a density reference table is stored in the memory 200. The density reference table shows unit change ratios (change ratios per the density 1%/m) corresponding to types of floating particles in several frequencies (for example, 82 kHz, 20 kHz), respectively. The smoke density estimator 180 refers to an unit change ratio corresponding to a estimated type of particles and estimates a smoke density.

TABLE 3

DENSITY TABLE

| FREQUENCY (kHz) | TYPES OF FLOATING PARTICLES | UNIT CHANGE RATIOS (CHANGE RATIO PER DENSITY 1%/m) |
|---|---|---|
| 82 | STEAM | 0.0075 |
|  | BLACK SMOKE | 0.0004 |
|  | WHITE SMOKE | 0.0012 |
| 20 | STEAM | 0.0040 |
|  | BLACK SMOKE | 0.0001 |
|  | WHITE SMOKE | 0.0001 |

Figure 5:
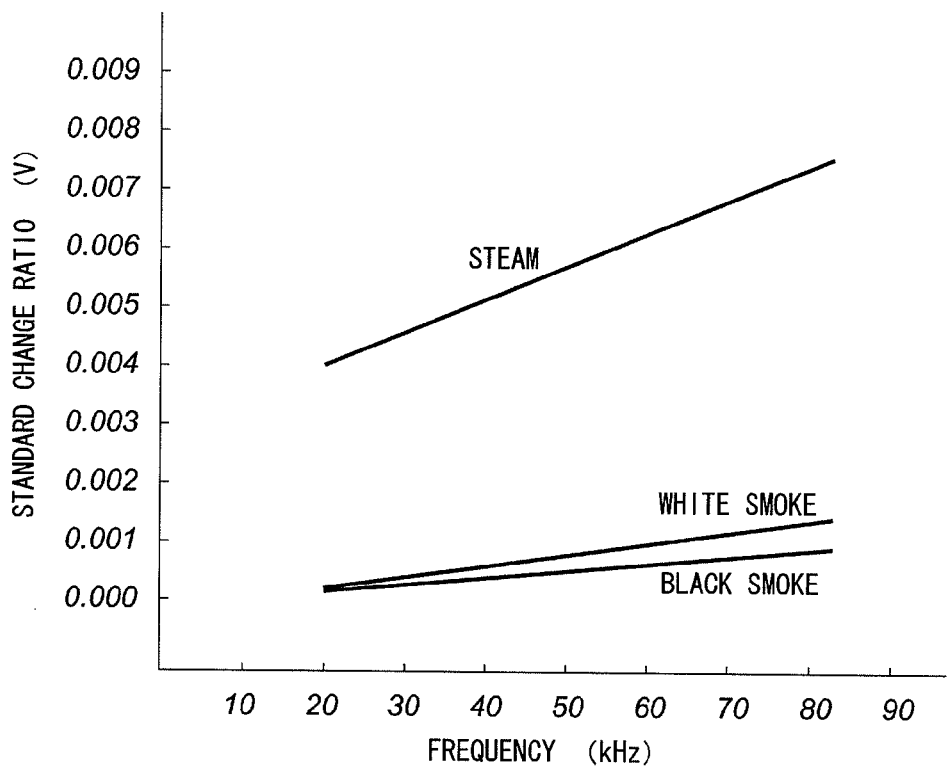
FIG. 5 is a graph explaining a method for estimating a density of each type of particles of a fire alarm system according to a first embodiment of the present invention.

Data stored in the density reference table is expressed with a graph shown in FIG. 5. The smoke density estimator 180 calculates a ratio between an actual change ratio measured in a standard frequency and an unit change ratio (a change ratio per the density 1%/m), in the standard frequency (here, 82 kHz), obtained from the density reference table, and this ratio is estimated as the smoke density.

Figure 6:
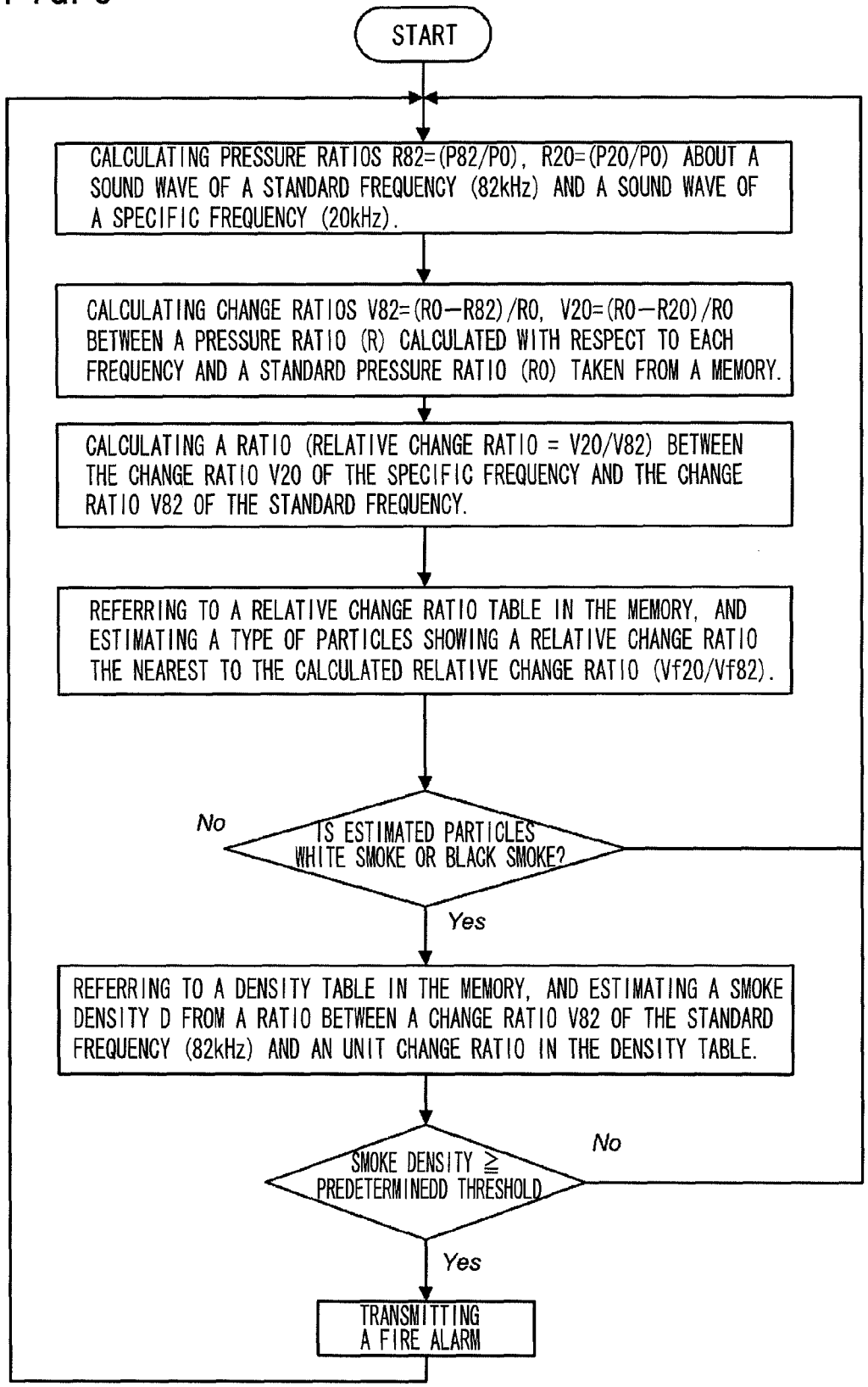
FIG. 6 is a flowchart explaining an operation of a fire alarm system according to a first embodiment of the present invention.

The fire alarm means determines existence of a fire and outputs a fire alarm if a type of smoke is black smoke or white smoke and the density exceeds a predetermined threshold (for example, 10%/m). The above mentioned performance is shown in a flowchart of FIG. 6. An arbitrary frequency can be used for the above mentioned standard frequency and specific frequency, and the frequency depending on when estimating the density isn't limited to the standard frequency, and a change ratio in specific frequency can be used. Furthermore, it is also possible to estimate the density based on an average value of the density which is calculated in two or more frequencies.

In the present embodiment, the particle estimator 170 of the above mentioned configuration is used. But it is not an indispensable condition that the fire alarm system of the present invention comprises the means of such configuration, and the smoke density can be also estimated from outputting of the change ratio of pressure ratio calculating means 160. In other words, as shown in FIG. 5, black smoke and white smoke by which a fire can be specified show the unit change ratios which are near each other. And the unit change ratio of steam unrelated to a fire shows a quite high value compared with black smoke and white smoke. So it is possible to omit the particle estimator if the fire alarm system isn't located at places (for example, the bathroom and kitchen) where steam generates so much to such an extent that a fire alarm is outputted. In this case, the densities of white smoke and black smoke, by which a fire can be specified, can be estimated by selecting an average vale or a representative value of the unit change ratio.

The pressure ratio correcting means 130 comprises an environment change correcting unit 140 and a reflection ratio correcting unit 150. The environment change correcting unit 140 corrects a pressure ratio in consideration of a change of an ultrasound wave's absorption loss associated with a change of ambient environment air. The reflection ratio correcting unit 150 corrects a pressure ratio produced with a change of the reflective performance of the first and second reflectors 50, 60.

The environment change correcting unit 140 is used with a temperature measuring means 142, a humidity measuring means 144 and an atmospheric pressure measuring means 146. The environment change correcting unit 140 receives temperature, humidity and atmospheric pressure measured by these means as atmosphere parameters. And then the environment change correcting unit 140 corrects a pressure ratio by using at least one of these parameters. On the other hand, the reflection ratio correcting unit 150 corrects a pressure ratio based on a reflection ratio calculated by a reflection change correcting means 152. It is not an indispensable condition that the fire alarm system of the present invention comprises the pressure ratio correcting means 130. But it is useful in order to achieve higher-accuracy fire detection. And it is preferred that at least one of the environment change correcting unit 140 and the reflection ratio correcting unit 150 is used.

(Explanation of Environment Change Correcting Unit 140)

First, the correction of a pressure ratio by the environment change correcting unit 140 is explained. An absorption loss in the air of a sound wave sent from the wave-generating element 20 and a change of a diffusion state of the sound wave are produced associated with changes of the atmospheric environment (temperature, humidity and atmospheric pressure) in the monitoring space even if smoke doesn't exist. So a first sound pressure and a second sound pressure show different change, respectively, since the propagation paths have different lengths, respectively. The first sound pressure is a sound pressure of a first sound wave which is directly propagated from the wave-generating element 20 to the wave-receiving element 30 through the first propagation path. The second sound pressure is a sound pressure of a second sound wave which is reflected by the reflectors 50, 60 and is propagated to the wave-receiving element. A sound pressure change ratio B associated with the absorption loss in the air is expressed with the following Formula 1 where x denotes a length of a propagation path, $\alpha_0$ denotes an absorption loss factor of the air in a standard state, and $\alpha_1$ denotes an absorption loss factor after changing of an air state.

$$B = \frac{e^{-\alpha_1 \cdot x}}{e^{-\alpha_0 \cdot x}} = e^{-(\alpha_1 - \alpha_0) \cdot x} \qquad \text{[Formula 1]}$$

Here, a change ratio of pressure ratio BR between the first and second sound waves by the above mentioned absorption loss can be expressed with the following Formula 2 where L denotes a length of the first propagation path of the first sound wave, and 3L denotes a length of the second propagation path of the second sound wave which is obtained by the reflection by the reflectors.

$$BR = \frac{e^{-(\alpha_1 - \alpha_0) \cdot 3L}}{e^{-(\alpha_1 - \alpha_0) \cdot L}} = e^{-(\alpha_1 - \alpha_0) \cdot 2L} \qquad \text{[Formula 2]}$$

Thus, a pressure ratio is changed by the above mentioned change ration of pressure ratio BR associated with a change of the absorption loss in the air. Here, it is know that the absorption loss factor is expressed with the function of air temperature, humidity, atmospheric pressure and a frequency of a sound wave, which are mediums. Since the frequency of the sound wave is determined by the controller, the change of the absorption loss can be calculated by air temperature, humidity and atmospheric pressure in the monitoring space.

Here, a sound speed V in the monitoring space is expressed with the following Formula 3 where T denotes air temperature, E denotes water vapor pressure, and P denotes atmospheric pressure in the monitoring space.

$$V = 20.067 \sqrt{T\left(1 + \frac{0.3192E}{P}\right)}$$ [Formula 3]

Therefore, air humidity H can be also calculated by the water vapor pressure E which is calculated by the function of the sound speed, the air temperature and the atmospheric pressure.

Then, a sound pressure and a pressure ratio receive influence in the directivity which shows a wavelength and a spread state of a sound wave, and the directivity is changed by a change of the wavelength. A wavelength λ of a sound wave, as shown in the following Formula 4, is determined by a frequency f and a sound speed V.

$$\lambda = \frac{V}{f}$$ [Formula 4]

Thus, it turns out that a wavelength of a sound wave depends on air temperature, humidity, atmospheric pressure and a frequency. The wavelength changes if air temperature, humidity and atmospheric pressure change from standard values, respectively. As a result, the directivity factor D, showing a wavelength and a spread state of a sound wave, changes, and then a sound pressure and a pressure ratio change.

The directivity factor D is expressed with the following Formula 5 where θ denotes an angle to a sending direction of a sound wave if the sound wave is a sine wave-like single pulse sound wave. And "a" in the Formula 5 denotes half the length of one side of a square which generation region of the wave-generating element 20 is formed into.

$$D(\theta) = \frac{\sin(2a\pi/\lambda \sin\theta)}{2a\pi/\lambda \sin\theta}, 0 \leq \theta \leq \sin^{-1}(\lambda/4a)$$

$$D(\theta) = \frac{1}{2a\pi/\lambda \sin\theta}, \sin^{-1}(\lambda/4a) \leq \theta \leq \pi/2a$$ [Formula 5]

So, if a wavelength change of a sound wave, i.e. a sound speed change in the air, i.e. air temperature, humidity and atmospheric pressure change from standard values, respectively, the directivity factor D changes. And then the sound pressures of the first and second sound waves also change, respectively. In addition, the first sound wave is directly received in the wave-receiving element 30 without the reflection by the reflectors. The second sound wave is reflected by the reflectors 50 and 60. Each of the reflectors 50 and 60 is formed into concave, and has an effect of collecting a sound. Thus, the second sound wave is received through a propagation path having a different length from the first sound wave's propagation.

The above mentioned absorption loss in the air and the change of the directivity have different influences on the sound pressures of the first and second waves, respectively. Then, the pressure ratio obtained based on these sound pressures changes. Therefore, the pressure ratio can be corrected by using air temperature, humidity and atmospheric pressure leading to these changes as parameters. In this correction, it's possible to correct individually based on the above mentioned relational expression. If for example, atmospheric pressure doesn't change, a change of temperature to a standard value is set to $\Delta T$, and a change of humidity is set to $\Delta H$, an amount of correction $\Delta PR$ of a pressure ratio between the sound pressures of the first and second sound wave is expressed with the following Formula 6. Influence associated with a change of atmospheric environment is corrected by using the following Formula 6 and adding the amount of correction $\Delta PR$ to a pressure ratio outputted from the calculation means 120.

$$\Delta PR = A1 \cdot \Delta T^2 + A2 \cdot \Delta T + A3 \cdot \Delta H^2 + A4 \cdot \Delta H + A5 \cdot \Delta T \cdot \Delta H + A6$$ [Formula 6]

In addition, the correction based on the change of environment isn't limited to the above mentioned formula, and a proper formula can be used.

And if a time lag between a time at which a sound wave is sent from the wave-generating element 20 and a time at which a sound wave is received in the wave-receiving element 30 is calculated and then a sound speed measuring means which calculates a sound speed by dividing a length of the propagation path by the time lag is adopted, the water vapor pressure E can be calculated based on the above mentioned Formula 3 and it's possible to calculate humidity from the water vapor pressure E. Therefore, if the fire alarm system comprises not only a thermistor, a thermocouple and a temperature sensor IC as the temperature measuring means 142 in the monitoring space but also the sound speed measuring means, the fire alarm system can calculate air humidity without comprising individual humidity detection elements as a humidity measuring means and it's possible to correct a pressure ratio based on temperature, humidity and atmospheric pressure of atmospheric environment.

(Explanation of Reflection Ratio Correcting Unit 150)

Reflection ratios of sound waves in the first and second reflectors 50, 60 change depending on a change of bulk modulus of the reflector's material and the matter adhering to the reflector's surface etc. In other words, because smoke is introduced into the monitoring space, the reflectors 50, 60 are exposed to the atmosphere of an installation site, and then the bulk modulus of the reflectors may change and dirt, such as dust and oil, may adhere on a reflection surface. In such a case, a reflection ratio of an ultrasound wave in the reflection surface may change, and then the pressure ratio $R_s$ calculated by the calculation means 120 may change from the default pressure ratio $R_0$ due to the change of the reflection ratio. Because the change of the pressure ratio due to the change of the reflection ratio is independent of the environment change correction, the reflection ratio correcting unit 150 determines a correction value of the pressure ratio $R_s$ and corrects the pressure ratio $R_s$ based on the correction value so that a changed part of the pressure ratio $R_s$ due to a change r'/r of the reflection ratio in the reflection surface is removed.

Consequently, the processing circuit 100 of the fire alarm system according to the present embodiment comprises the reflection change correcting means 152 and the reflection ratio correcting unit 150. The reflection change correcting means 152 calculates a value relevant to the reflection ratio of the ultrasound wave in the reflection surface. The reflection ratio correcting unit 150 corrects a pressure ratio based on a change of the reflection ratio calculated by the reflection change correcting means 152.

Figure 7:
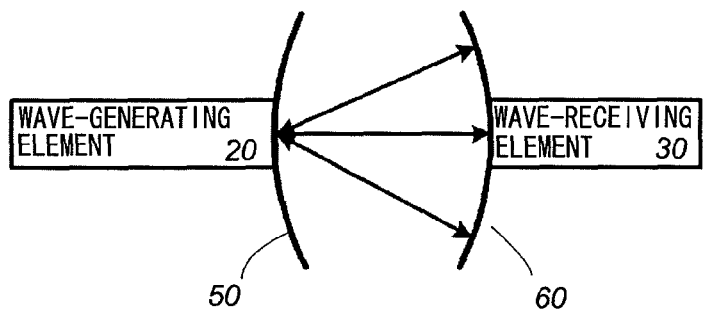
FIG. 7 is a schematic explaining propagation paths having different lengths of a detection unit of a fire alarm system according to a first embodiment of the present invention.
Figure 8:
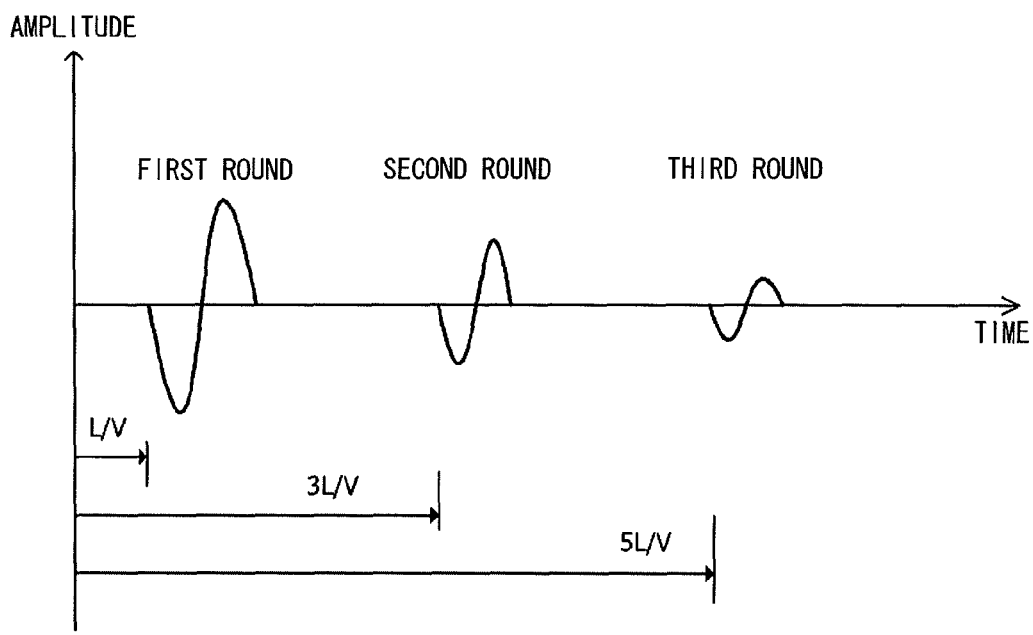
FIG. 8 is a schematic showing ultrasound waves received through propagation paths having different lengths of a fire alarm system according to a first embodiment of the present invention.

The reflection change correcting means 152 calculates the change of the reflection ratio, based on pressure ratios of sound waves which are propagated through the propagation paths having the different lengths while reflecting by the reflectors and is received in the wave-receiving element 30 in the monitoring space. In other words, as shown in FIG. 7, in addition to a first propagation path (length L) and a second propagation path (length 3L), a third propagation path (length 5L) is set. The first propagation path is a path through which a sound wave is directly propagated from the sound wave generator 20 to the wave-receiving element 30. The second propagation path is a path through which a sound wave is propagated to the wave-receiving element 30 after reflection by the second and first reflectors 60, 50. The third propagation path is a path through which a sound wave is propagated to the wave-receiving element 30 after the sound wave is reflected two times by the second and first reflectors 60, 50, respectively. Sound pressures $P_{10}$, $P_{20}$, $P_{30}$ corresponding to the first, second and third propagation paths, respectively are calculated. These sound waves, as shown in FIG. 8, are received in the wave-receiving element 30 after times, which is obtained by dividing the lengths of the propagation paths by a sound speed, from a sound wave's generating time (t=0), respectively.

A relative change ratio of the reflection r' to a default value r is expressed with r'/r where r denotes a default value of a reflection ratio of an ultrasound wave in the reflection surface, and r' denotes a present reflection ratio'. A sound pressure of the ultrasound wave, which is reflected once or more by the reflection surface and then reaches the wave-receiving element 3, changes corresponding to the above mentioned change ratio r'/r. A change of this sound pressure is expressed by raising r'/r to the power of reflection times (that is, it is expressed with $(r'/r)^n$ when the number of reflection times is n times). In other words, the sound pressure $P_{20}'$ of the second sound wave, which reaches the wave-receiving element through the second propagation path, is expressed with $P_{20}'=P_{20}(r'/r)^2$. Therefore, a pressure ratio $R_{20}'$ between a sound pressure of a sound wave, which is propagated through the first propagation path (the number of reflection times is 0 times), and a sound pressure of a sound wave, which is propagated through the second propagation path, is expressed with the following Formula 7.

$$R'_{20} = \frac{P'_{20}}{P_{10}} = \frac{P_{20} \cdot (r'/r)^2}{P_{10}} \quad \text{[Formula 7]}$$

Thus, if the reflection ratio of the ultrasound wave in the reflection surface changes, the pressure ratio $R_s$ between sound waves, which are propagated through the first and second propagation paths, respectively, changes regardless of the smoke density.

Similarly, a sound pressure $P_{30}'$ of a sound wave which is propagated through the third propagation path (the number of reflection times is 4 times) is expressed with $P_{30}'=P_{30}(r'/r)^4$ where $P_{30}$ is a default value. Therefore, a pressure ratio $R_{30}'$ between a sound pressure of a sound wave, which is propagated through the first propagation path (the number of reflection times is 0 times), and a sound pressure of a sound wave, which is propagated through the third propagation path, is expressed with the following Formula 8.

$$R'_{30} = \frac{P'_{30}}{P_{10}} = \frac{P_{30} \cdot (r'/r)^4}{P_{10}} \quad \text{[Formula 8]}$$

By the way, a sound pressure ($P_s$) of a sound wave which is propagated through each of the propagation paths is expressed with $P_s=P_0(1-\alpha \cdot C \cdot L)$ where C[%/m] denotes a smoke density by the above mentioned light extinction system in the monitoring space, a denotes a loss ratio of an ultrasound wave of per 1 [m] to the smoke density 1 [%/m], and L[m] denotes a length of a propagation path of an ultrasound wave. Here, $P_0$ is a sound pressure of a sound wave outputted from the sound wave generator and is a known value set up previously. The loss ratio α is a value related with the density C in a smoke density detection method standardized previously. The length of the first and second propagation paths is expressed with (n+1)·L by using the number of reflection times (n). In other words, the length of the second propagation path, of which the number of reflection times is 2 times, is expressed with 3L, and the length of the third propagation path, of which the number of reflection times is 4 times, is expressed with 5L. Therefore, the reflection change correcting means 152 calculates a reflection change ratio (r'/r), substituting $P_{10}=P_0(1-\alpha \cdot C \cdot L)$, $P_{20}=P_0(1-\alpha \cdot C \cdot 3L)$, $P_{30}=P_0(1\alpha \cdot C \cdot 5L)$ into the above mentioned Formula 7, 8. The reflection ratio correcting unit 150 corrects pressure ratios ($R_{10}'$, $R_{20}'$) based on the calculated reflection change ratio, and calculates pressure ratios ($R_{10}$, $R_{20}$) from which change parts of pressure ratios depending on the reflection change ratio (r'/r) are removed, respectively, and outputs this corrected pressure ratios into the change ratio of pressure ratio calculating means 160.

Therefore, the change of reflection ratio due to aging degradation and dirt of the reflection surface can be canceled, and the above mentioned estimation of particles type, estimation of the smoke density and determination of a fire associated with this can be performed more accurately.

Figure 9:
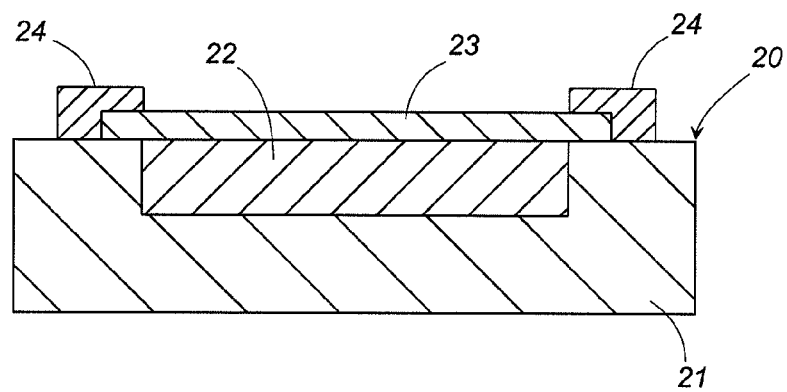
FIG. 9 is a cross-section view showing an example of a wave-generating element achieving a sound wave generator used in a fire alarm system according to a first embodiment of the present invention.

In the system, the wave-generating element 20, which has the configuration as shown in FIG. 9, is used as the sound wave generator. This wave-generating element 20 comprises a baseboard 21 constructed of p-type silicon of a single crystal, a heat insulation layer 22, which is a porous silicon layer, formed at a part of the top surface of the baseboard 21, a heating element layer 23, which is a metal thin film, formed on the surface side of the heat insulation layer 22, and a pair of pads 24, 24 electrically connected with the heating element layer 23 on the top surface side of the baseboard 21. A planar shape of the baseboard 21 is a rectangle. Planar shapes of the heat insulation layer 22 and the heating element layer 23 are also rectangles, respectively. In the top surface side of the baseboard 21, an insulation film (not shown) comprising a silicon dioxide film is formed on the surface of a portion at which the heat insulation layer 22 is not formed.

The above mentioned controller 40 makes the heating element layer 23 produce a rapid change in temperature by supplying a voltage to the pads 24, 24 of both ends of the heating element layer 23. This makes the air (medium) in contact with the heating element layer 23 produce a rapid change in temperature (thermal shock). The air in contact with the heating element layer 23 expands with increase in temperature of the heating element layer 23 and contracts with decrease in temperature of the heating element layer 23, so the ultrasound wave which is propagated through the air is generated by controlling suitably energization of the heating element layer 23. Thus, since the ultrasound wave propagated through the medium is generated by converting a rapid change in temperature of the heating element layer 23 associated with energization of the heating element layer 23 into expansion or contraction of the medium, the ultrasound wave with little reverberation can be sent compared with the case where the ultrasound wave is generated by mechanical vibration like a piezo element.

In the above mentioned wave-generating element 20, the p-type silicon substrate is used as the baseboard 21 and the heat insulation layer 22 consists of a porous silicon layer of which a porosity is nearly 60% to 70%. The porous silicon layer is formed by anodizing a part of a silicon substrate in an electrolysis solution which is a mixed solution of a hydrogen fluoride solution and ethanol. The porous silicon layer formed by anodizing contains much nano crystal silicon being fine crystal silicon of which crystal grain size is nanometer scale. A heat thermal conductivity and a heat capacity of the porous silicon layer become small as the porosity becomes high, so the heat thermal conductivity and the heat capacity of the heat insulation layer 22 can be made small compared with the heat thermal conductivity and the heat capacity of the baseboard 21. And the product of the heat thermal conductivity and the heat capacity of the heat insulation layer 22 can be made small enough compared with the product of the heat thermal conductivity and the heat capacity of the baseboard 21. As a result, the change in temperature of the heating element layer 23 can be efficiently transmitted to the air, and efficient heat exchange can be generated between the heating element layer 23 and the air. At the same time, the baseboard 21 efficiently receives the heat from the heat insulation layer 22 and can lose the heat and then it can prevent that the heat is accumulated in the heat insulation layer 12.

As for a porous silicon layer, of which a porosity is 60%, formed by anodizing a silicon substrate of a single crystal of which the heat thermal conductivity and the heat capacity are 148 W/(m·k), $1.63 \times 10^6$ J/(m$^3$·K), respectively, it is known that the heat thermal conductivity and the heat capacity are 1 W/(m·k), $0.7 \times 10^6$ J/(m$^3$·K), respectively. In the present embodiment, the heat insulation layer 22 consists of a porous silicon layer of which a porosity is nearly 70%, and the heat thermal conductivity and the heat capacity of the heat insulation layer 12 are 0.12 W/(m·k), $0.5 \times 10^6$ J/(m$^3$·K), respectively.

Although the heating element layer 23 is formed with tungsten which is a kind of a high melting point metal, a material of the heating element layer 23 isn't limited to tungsten, and for example, tantalum, molybdenum, iridium, aluminum, etc. may be adopted as the material. A thickness of the baseboard 21 is 300 μm to 700 μm, and a thickness of the heat insulation layer 22 is 1 μm to 10 μm, and a thickness of the heating element layer 23 is 20 nm to 100 nm, and a thickness of the pad 24 is 0.5 μm. Such thickness is an example and is not especially limited. Moreover, although Si is adopted as a material of the baseboard 21, not only Si but other semiconducting material may be sufficient as the material of the baseboard 21. The other semiconducting material is, for example, Ge, SiC, GaP, GaAs and InP, etc. and can have porous configuration by anodizing. And in each case, a porous layer which is formed by anodizing a part of the baseboard 21 can be set to the heat insulation layer 22.

The above mentioned wave-generating element 20 generates an ultrasound wave due to a change in temperature of the heating element layer 23 associated with energization of the heating element layer 23. If an drive input waveform from the controller 40 is a sine wave of which a frequency is f1, a frequency of temperature oscillation produced in the heating element layer 23 becomes f2 which is twice f1. So an ultrasound wave having a frequency which is nearly twice the drive input waveform f1 can be generated. Thus, the wave-generating element 20 of the above mentioned configuration has a flat frequency characteristic, and a frequency of an ultrasound wave generating can be changed over a wide range.

Figure 10A:
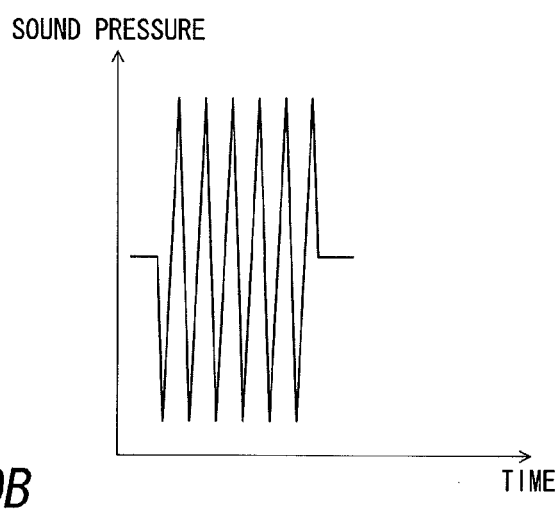
FIG. 10 is an illustration showing an example of a method generating an ultrasound wave having a plurality of frequencies from a wave-generating element of a fire alarm system according to a first embodiment of the present invention.
Figure 10B:
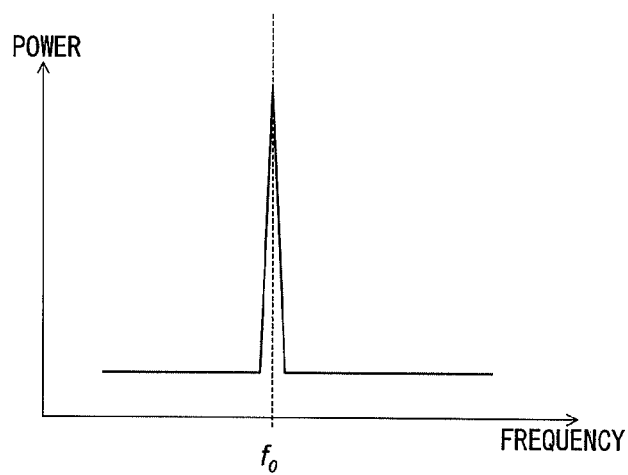

In order to make an ultrasound wave having several different frequencies output from the above mentioned wave-generating element 20, the controller 40, as shown in FIG. 10A, operates about each of the frequencies so that a burst wave of a continuous wave (for example, three cycles) having a predetermined frequency f0 is outputted. In this case, as shown in FIG. 10B, there is a peak in a frequency f0 according to the number of cycles, and intensity becomes low in other frequency bands, and each of the frequencies can be distinguished clearly. In addition, because the heat insulation layer 22 consists of a porous layer, heat insulating properties of the heat insulation layer 22 is improved, and ultrasound wave generating efficiency becomes high, and power consumption can be decreased compared with the case where the heat insulation layer 22 consists of a non-porous layer (for example, SiO$_2$ film etc.).

Figure 11:
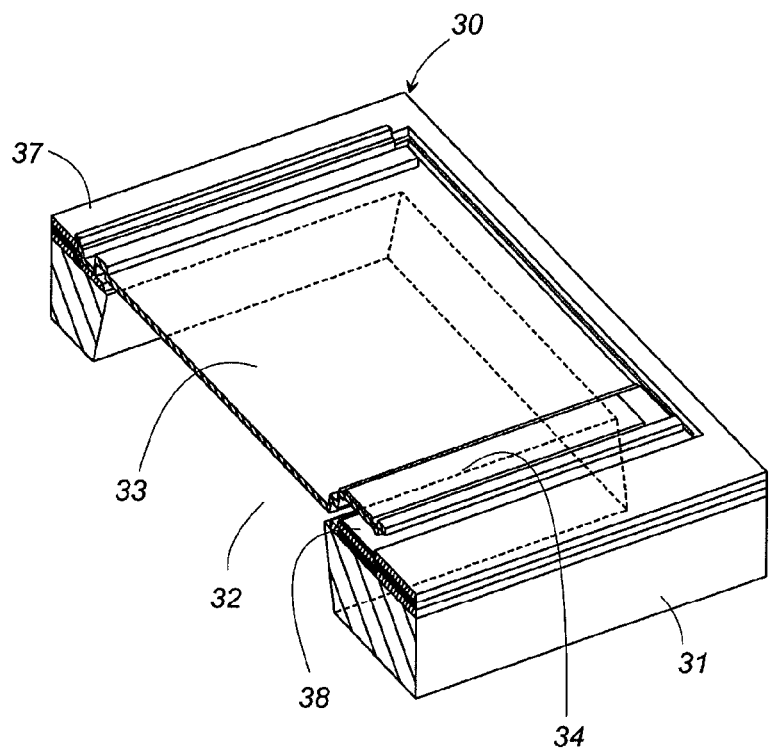
FIG. 11 is a perspective view showing an example of a wave-receiving element achieving a sound wave detector used in a fire alarm system according to a first embodiment of the present invention.
Figure 12:
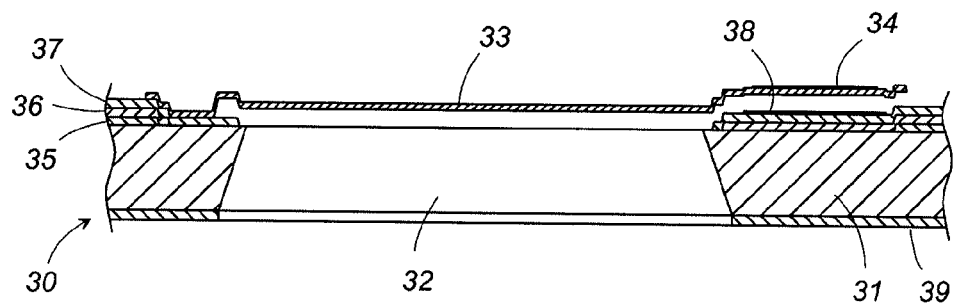
FIG. 12 is a cross-section view of a wave-receiving element shown in FIG. 11.

As shown in FIGS. 11 and 12, a capacitance type microphone is used as the wave receiving element 30 which is a sound wave detector. This element comprises a frame 31, which is a silicon substrate formed in the shape of a rectangle, comprising a window-hole 32, and a cantilever type vibrating membrane 33 located at a surface side of the frame 31 so as to straddle two sides facing each other. A thermally-oxidized film 35, a silicon dioxide film 36 covering the thermally-oxidized film 35, and a silicon nitride film 37 covering the silicon dioxide film 36 are formed in the surface side of the frame 31. A fixed end of the vibrating membrane 33 is supported by the frame 31 through the silicon nitride film 37, and a free end of the vibrating membrane 33 is located so as to face the silicon nitride film 37. A fixed electrode 38 which consists of a metal thin film (for example, chromium film etc.) is formed in the silicon nitride film 37 corresponding to the free end of the vibrating membrane 33. A movable electrode 34 which consists of a metal thin film (for example, chromium film etc.) is formed on a surface of the opposite side of a surface facing the silicon nitride film 37 in the free end of the vibrating membrane 33. In addition, a silicon nitride film 39 is formed in the under surface of the frame 31. And the vibrating membrane 33 comprises a silicon nitride film formed at a process other than a process in which the above mentioned silicon nitride films 37, 39 are formed.

In the wave receiving element 30 which is a capacitance type microphone having the above mentioned configuration, a capacitor using the fixed electrode 38 and the movable electrode 34 as a pair of electrodes is formed, so a distance between the fixed electrode 38 and the movable electrode 34 changes and an electric capacity between both electrodes changes when the vibrating membrane 33 receives a pressure of a longitudinal wave. A tiny change of voltage is produced between both electrodes depending on a sound pressure of an ultrasound wave when a direct current bias voltage is supplied between both electrodes, and then the sound pressure of the ultrasound wave is changed into an electric signal by taking out this change of voltage. Consequently, each of the fixed electrode 38 and the movable electrode 34 is connected to a source of voltage through a resistor, and the above mentioned sound pressure detector 110 detects a voltage in both ends of this resistor to read a sound pressure as an electric signal.

Figure 13:
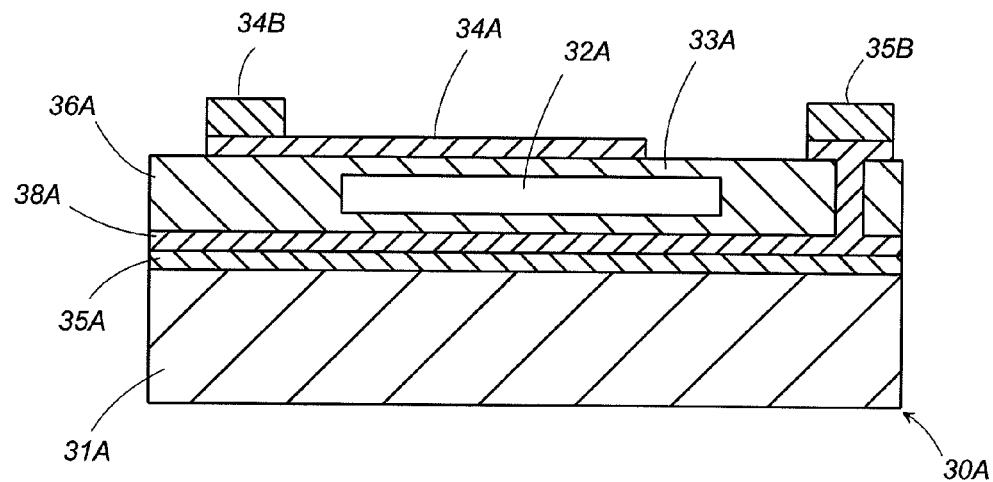
FIG. 13 is a cross-section view of other wave-receiving element used in a fire alarm system according to a first embodiment of the present invention.

FIG. 13 shows the wave-receiving element 30A having other configuration which can be used for the system of the present invention, and this wave-receiving element is configured to combine a function of the above mentioned atmospheric pressure measuring means 146. This element is configured to laminate an insulation film 35A, a fixed electrode 38A of a metal thin film, and an insulation layer 36A on a surface of a silicon substrate 31A. A standard pressure room 32A of which atmospheric pressure is maintained constant is formed in the insulation layer 36A, and a part of the insulation layer 36A located between the standard pressure room 32A and a monitoring space is specified as a vibrating membrane 33A. A movable electrode 34A is formed in the top surface of this vibrating membrane 33A. If an ultrasound wave is received, the vibrating membrane 33A vibrates and a distance between the movable electrode 34A and the fixed electrode 38A changes and an electric capacity between both electrodes changes.

In this wave-receiving element 30A, a direct current bias voltage is supplied between both pads 35B, 34B which are located at the fixed electrode 35A and the movable electrode 34A, respectively. A tiny change of voltage, which is produced between both pads according to a sound pressure of an ultrasound wave, is taken out as an output showing the sound pressure. A direct current component, which this change of voltage comprises, corresponds to a difference of atmospheric pressure between the standard pressure room 32A and the monitoring space. For this reason, the direct current component can be used as an output showing atmospheric pressure of the monitoring space. In this configuration, the atmospheric pressure of the monitoring space can be measured by using a change of the electric capacity between the fixed electrode 35A and the movable electrode 34A, and it isn't necessary to newly set up a pressure sensor etc. for measuring atmospheric pressure, and component count of the fire alarm system can be reduced.

The controller 40 controls a sending operation of an ultrasound wave from the wave-generating element 20 and a receiving operation of the ultrasound wave in the wave-receiving element 30. Controlling of the sending operation is achieved by a drive circuit for giving a drive input waveform to the wave-generating element 20 and driving the wave-generating element 20, and a microcomputer for controlling the drive circuit. A sound wave having a predetermined frequency is intermittently sent from the wave-generating element. Controlling of the receiving operation is achieved by a drive circuit for supplying a bias voltage to drive the wave-receiving element 30, and a microcomputer. The microcomputer controls the wave-receiving element so as to be synchronized with a timing to which the sent sound wave is propagated through the air and reaches the wave-receiving element, and to send a sound wave signal to a processing circuit. The sound wave signal is intermittently sent to the processing circuit 100. In order to receive ultrasound waves propagated through propagation paths having different lengths, respectively, a predetermined period around a receiving timing corresponding to the length of propagation path is set as a receiving period.

Figure 14:
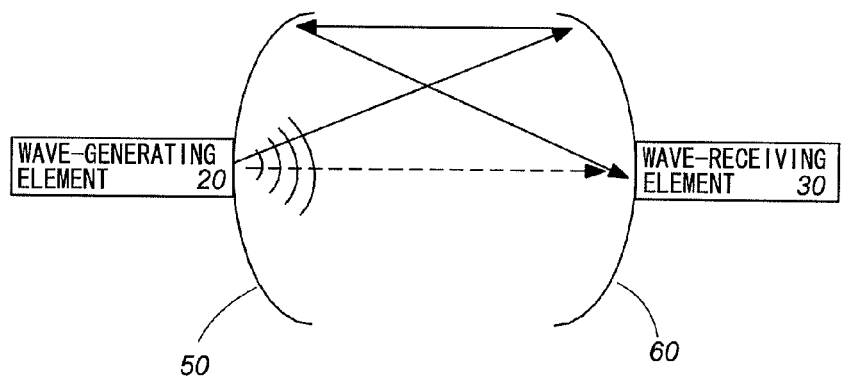
FIG. 14 is a schematic showing other detection unit used in a fire alarm system according to a first embodiment of the present invention.

In the detection unit 10 comprising the first and second reflectors 50, 60, a configuration of comprising each of the reflectors, as shown in FIG. 14, which curves in the shape of paraboloidal surface along own length direction can be used other than a configuration of comprising each of the reflectors, as shown in FIG. 7, which has an uniform curvature. In this case, a length of a propagation path through which a sound wave is reflected by the reflector and reaches the wave-receiving element 30 is set as the integral multiple of a length of a propagation path L through which a sound wave is directly propagated from the wave-generating element to the wave-receiving element 30.

Second Embodiment

Figure 15:
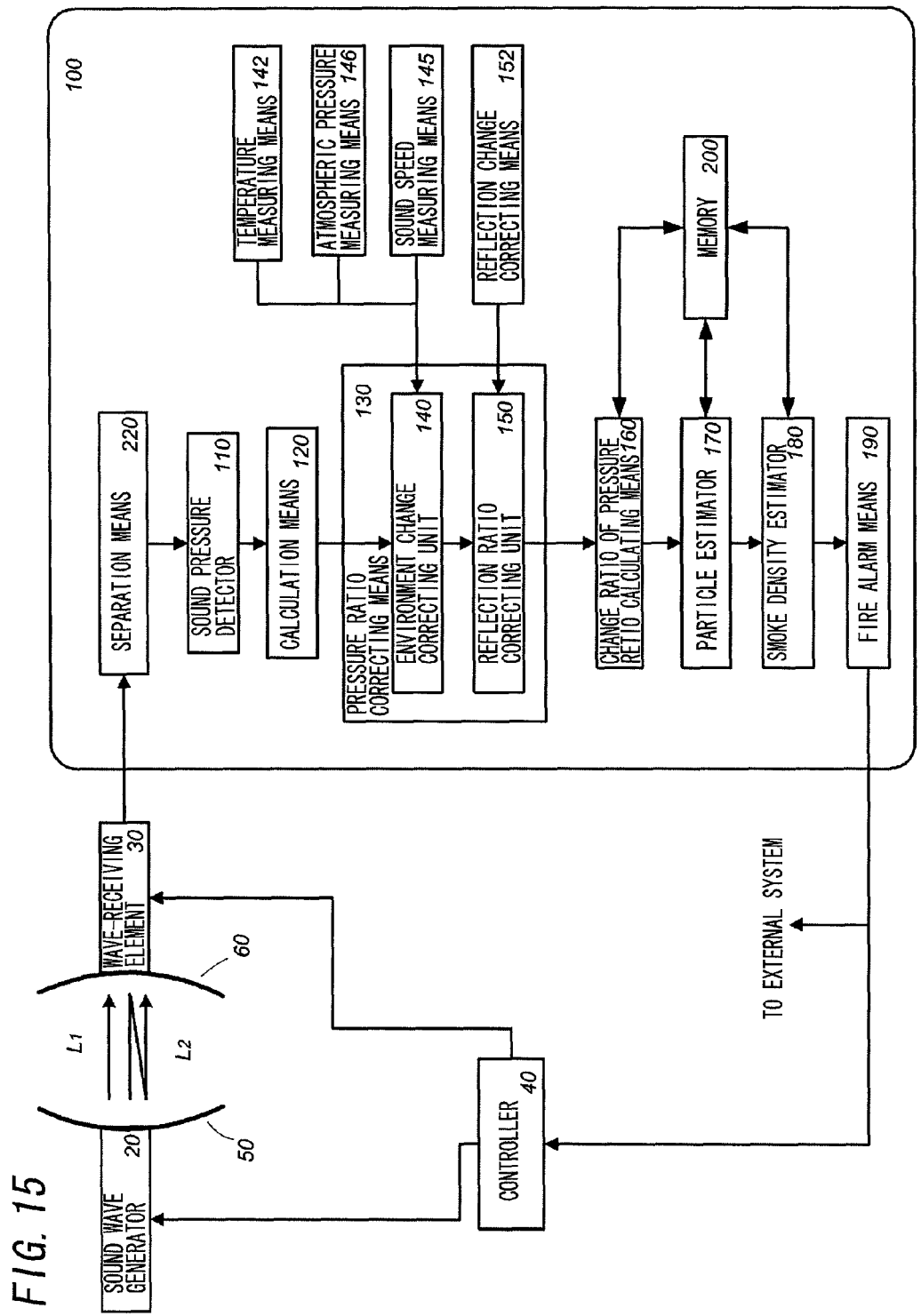
FIG. 15 is a schematic showing a fire alarm system according to a second embodiment of the present invention.

FIG. 15 shows a fire alarm system according to a second embodiment of the present invention. The system differs from the above mentioned first embodiment in that a sound wave generator 20 generates an ultrasound wave comprising a plurality of frequency components and a separation means 220 for separating the plurality of frequency components is formed in the processing circuit 100. Other configuration and actions of the system are basically the same as that of the first embodiment. In the second embodiment, a sound speed measuring means 145 is used and the system is configured to calculate humidity of the monitoring space.

Figure 16A:
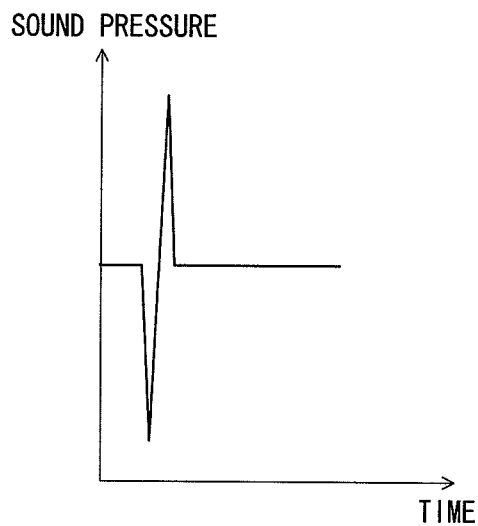
FIGS. 16A and 16B are schematics explaining an operation when using a single pulse outputted from a wave-generating element.
Figure 16B:
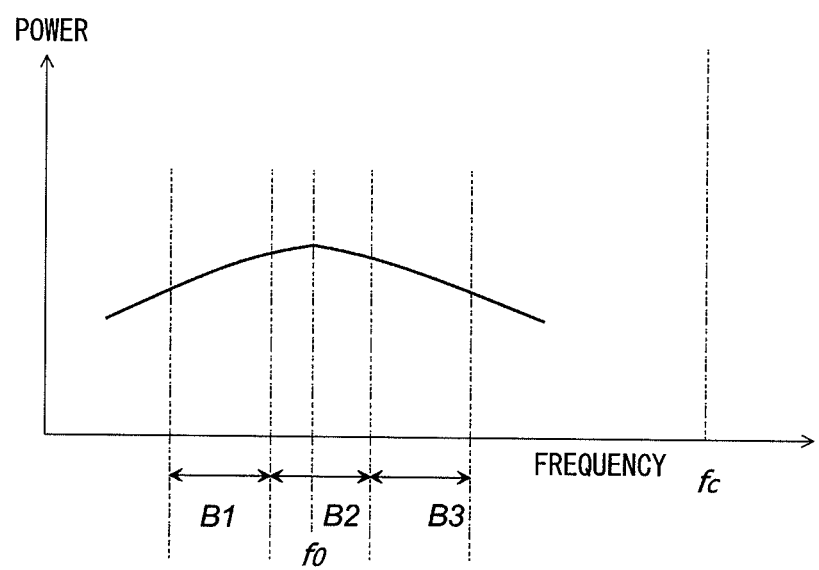

In order to make an ultrasound wave comprising the plurality of frequency components send from a wave-generating element 20 which is the sound wave generator, a controller 40 of the second embodiment gives a drive input wave form which is a solitary wave of half sine to the wave-generating element 20. An ultrasound wave of a single pulse of nearly 1 cycle, as shown in FIG. 16A, is outputted from the wave-generating element 20. Intensity (energy) of a power spectrum of this ultrasound wave, as shown in FIG. 16B, is distributed over a wide range of frequency, by setting a frequency f0 according to a pulse width into a center frequency. And then the ultrasound wave comprising the plurality of frequency components is outputted from the wave-generating element 20. For this reason, the separation means 220 is configured to extract the intensity of a frequency component about each of frequency bands as shown in B1 to B3 of FIG. 16B.

On the other hand, the capacitance type microphone, of which Q value of a resonance characteristic is small enough compared with a piezo element, is used as the wave-receiving element 30. So there is no great variability in sensitivity about the plurality of frequency components which the ultrasound wave sent from the wave-generating element 20 comprises. However, the sensitivity falls in a frequency band higher than a resonance frequency fc of the wave-receiving element 30, so it's preferred that the wave-receiving element 3 has the resonance frequency higher than the frequency bands B1 to B3 where the intensity of the frequency component is extracted by the separation means 220.

Figure 17A:
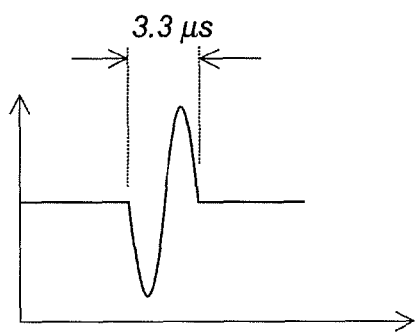
FIGS. 17A and 17B are schematics explaining a frequency separation of a single pulse, shown in FIGS. 16A and 16B, detected in a wave-receiving element
Figure 17B:
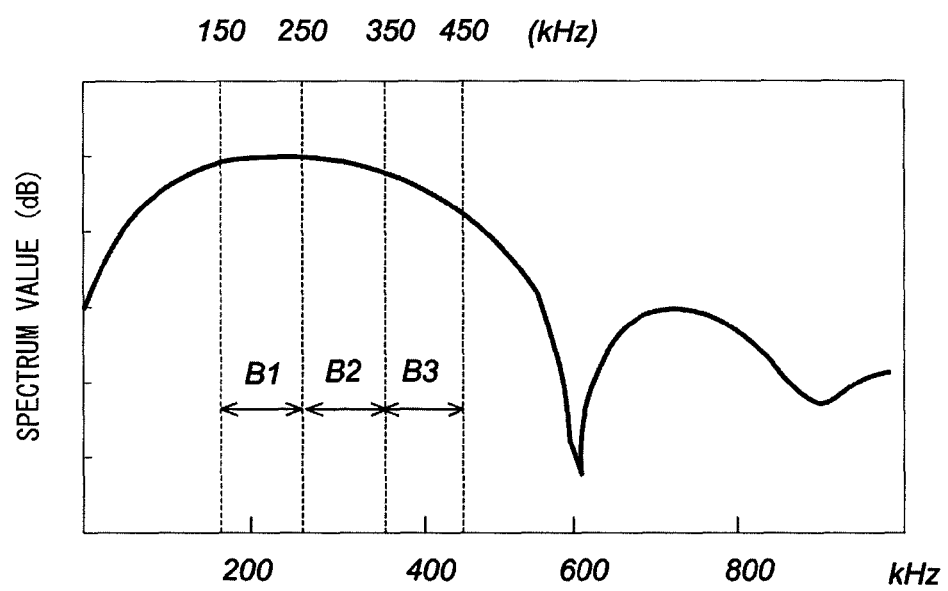
Figure 18:
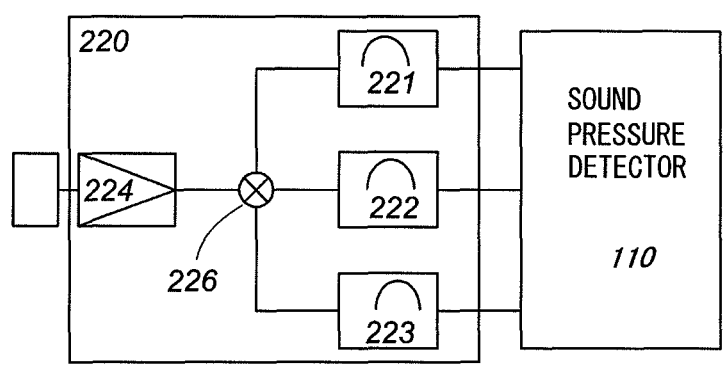
FIG. 18 is schematic of a separation means for separating frequency shown in FIGS. 17A and 17B

Next, a configuration of the separation means 220 is explained. For example, it is assumed that when an ultrasound wave of a single pulse of which a cycle is 3.33 μs (300 kHz) as shown in FIG. 17A is sent from the wave-generating element 20, a power spectrum of the ultrasound wave received in the wave-receiving element 30 has a peak in 300 kHz as shown in FIG. 16B. In this case, in order to extract the intensity of each frequency component of frequency bands B1 to B3 in FIG. 17B, the separation means 220, as shown in FIG. 18, comprises a first filter 221 letting a signal of 150 kHz to 250 kHz (frequency band B1) pass through, a second filter 222 letting a signal of 250 kHz to 350 kHz (frequency band B2) pass through, and a third filter 223 letting a signal of 350 kHz to 450 kHz (frequency band B3) pass through. The separation means 220 takes out an output of each of the first, second and third filters as the intensity of each of frequency components, and outputs to the sound pressure detector 110. The separation means 220 also comprises an amplifier 224 amplifying an output of the receiving element 30, and a distribution means 226 distributing the output amplified by the amplifier to each of the filters. Thus, the separation means 220 can extract the intensity of the plurality of frequency components from the ultrasound wave which is sent from the wave-generating element 20 at once.

In addition, in order to make the wave-generating element 20 send the ultrasound wave comprising the plurality of frequency components, it isn't limited to the above mentioned ultrasound wave of a single pulse, and it is possible to control the wave-generating element by the controller 40 to generate an ultrasound wave which is few burst wave of a cycle or an ultrasound wave which is formed by superimposing several ultrasound waves having different frequencies each other.

In the present embodiment, the controller 40 gives the drive input wave form which is a solitary wave of half sine to the wave-generating element 20, and an ultrasound wave with little reverberation of a single pulse of nearly 1 cycle is generated. By using such ultrasound wave of a single pulse, reflection interference can be inhibited.

Figure 19:
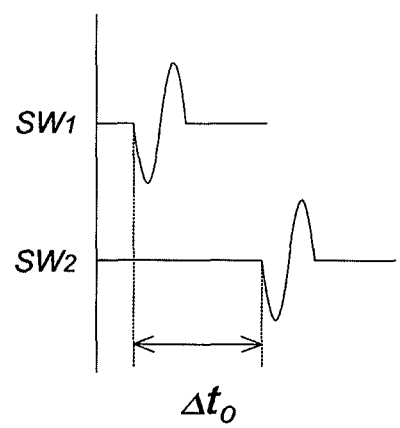
FIG. 19 is a waveform chart explaining measurement of a sound speed by a sound speed measuring means used in a fire alarm system according to a second embodiment of the present invention.

In the present embodiment, the sound speed measuring means 145 is used, and humidity in atmospherics is estimated based on a sound speed calculated in the sound speed measuring means 145, and the environment change correcting unit 140 is configured to correct a pressure ratio depending on a change of atmosphere environment, based on humidity calculated in the temperature measuring means 142 and the sound speed measuring means 145. The sound speed measuring means 145, as shown in FIG. 19, is configured to calculate a time difference $\Delta t_0$ between a receiving timing of a sound wave SW1 propagated through the first propagation path and a receiving timing of a sound wave SW2 propagated through the second propagation path, and to calculate the sound speed V by dividing a difference ($L_2-L_1$) between the lengths of the first and second propagation paths by the time difference $\Delta t_0$. And humidity can be calculated by using Formula 3 explained in the first embodiment. Or a sound wave can be calculated by dividing the length ($L_1$) of the first propagation path and the length ($L_2$) of the second propagation path by a time difference between a timing of generating a sound wave and a timing of receiving the sound wave.

Although the present invention has been described with reference to certain preferred embodiments, numerous modifications and variations can be made by those skilled in the art without departing from the true spirit and scope of this invention, namely claims.

The invention claimed is:

1. A fire alarm system comprising:
   a sound wave generator sending a sound wave;
   a sound wave detector being located so as to sandwich in a monitoring space between itself and the generator, the sound wave detector detecting the sound wave sent from the generator through the monitoring space;
   a controller being configured to control the generator and the sound wave detector;
   a processing circuit being configured to process an output detected by the sound wave detector, the processing circuit comprising a sound pressure detector for detecting a sound pressure based on the output, a smoke density estimator for estimating a density of smoke existing in the monitoring space and a fire alarm device being configured to transmit fire alarm when the smoke density estimated by the smoke density estimator exceeds a predetermined threshold;
   wherein the generator and the sound wave detector are located in the monitoring space so as to form a first and second propagation paths for propagating the sound wave from the generator to the sound wave detector, the first and second propagation paths having different lengths from each other,
   wherein the processing circuit comprises a calculation means for calculating a pressure ratio between a first sound pressure being a sound pressure of a sound wave propagated through the first propagation path and a second sound pressure being a sound pressure of a sound wave propagated through the second propagation path,
   wherein the smoke density estimator is configured to calculate a change ratio between the pressure ratio calculated by the calculation means and a predetermined average pressure ratio, and to determine the smoke density from the change ratio based on a predetermined relational expression, the relational expression describing the change ratio in relation to the smoke density,
   wherein the first and second propagation paths extend from the same generator to the same sound wave detector.

2. A fire alarm system as claimed in claim 1, wherein the generator is configured to send a single sound wave having a first and second frequency components differing from each other,
   wherein the processing circuit comprises a separation means for separating the first and second frequency components,
   wherein the sound pressure detector is configured to detect sound pressures about the first and second frequency components, respectively,
   wherein the processing circuit comprises a particle estimator for estimating a type of floating particles based on the pressure ratio outputted from the calculation means,
   wherein the particle estimator is configured to calculate a relative change ratio between a first change ratio and a second change ratio, the first and second change ratios being calculated in reference to the first and second frequency components, respectively,
   wherein the processing circuit comprises a memory for storing a relative change ratio table and a density table, the relative change ratio table having different relative change ratios corresponding to different types of floating particles, the density table having different smoke densities corresponding to different first change ratios,
   wherein the particle estimator is configured to estimate a type of floating particles, corresponding to the relative change ratio, in the relative change ratio table,
   wherein the smoke density estimator is configured to estimate a smoke density, corresponding to the first change ratio, in the density table if the type of floating particles is smoke.

3. A fire alarm system as claimed in claim 2, wherein the generator is configured to generate a sound wave of as single pulse.

4. A tire alarm system as claimed in claim 2, wherein the separation means comprises frequency filters letting sound waves of the first and second frequency components pass through, respectively,
   wherein the calculation means is configured to calculate the pressure ratio about the sound waves or the first and second frequency components passing through the frequency filters.

5. A fire alarm system as claimed in claim 1, wherein the generator comprises a single wave-generating element,
   wherein the sound wave detector comprises a single wave-receiving element,
   wherein the first and second propagation paths are formed between a first reflector located at the side of the wave-generating element and a second reflector located at the side of wave-receiving element,
   wherein the first propagation path is set as the shortest straight path between the wave-generating and wave-receiving elements,
   wherein the second propagation path is set as a reflex path through which a sound wave sent from the wave-generating element is reflected by the second reflector and the first reflector and is leaded to the wave-receiving element.

6. A tire alarm system as claimed in claim 1, wherein the processing circuit comprises a parameter measuring means for measuring at least one parameter of air temperature, humidity and atmospheric pressure, and an environment change correcting means for correcting a change of the pressure ratio depending on an environment change based on the parameter.

7. A fire alarm system as claimed in claim 6, wherein the processing circuit comprises a sound speed measuring means for measuring a sound speed in the monitoring space by dividing a length of the first propagation path by a time difference between a timing of detecting the first sound pressure and as timing of driving the generator, wherein the environment change correcting means is configured to correct the change of the pressure ratio depending on the environment change based on the sound speed.

8. A fire alarm system as claimed in claim 5, wherein in addition to the first and second propagation paths, a third propagation path for propagating a sound wave is formed between the first and second reflectors, wherein the number of reflection times of a sound wave propagated through the second propagation path to the wave-receiving element is more than the number of reflection times of a sound wave propagated through the first propagation path to the wave-receiving element, and is less than the number of reflection times of a sound wave propagated through the third propagation path to the wave-receiving element, wherein the processing circuit comprises a reflection change calculating means for calculating a relative change ratio for a default value about reflective performance in the reflectors, based on a pressure ratio among the first sound pressure obtained by receiving the sound wave propagated through the first propagation path, the second sound pressure obtained by receiving the sound wave propagated through the second propagation path and a third sound pressure obtained by receiving the sound wave propagated through the third propagation path, which are different from each other in the number of reflection times, and a reflection change correcting means for correcting the pressure ratio based on the relative change ratio calculated by the reflection change calculating means.

9. A fire alarm system as claimed in claim 1, wherein the generator is configured to send sound waves having a first and second frequencies differing from each other, respectively, wherein the processing circuit comprises a particle estimator for estimating a type of floating particles based on the pressure ratio outputted from the calculation means, wherein the particle estimator is configured to calculate a relative change ratio between a first change ratio and a second change ratio, the first and second change ratios being calculated in reference to the sound waves of the first and second frequencies, respectively, wherein the processing circuit comprises a memory for storing a relative change ratio table and a density table, the relative change ratio table having different relative change ratios corresponding to different types of floating particles, the density table having different densities of smoke corresponding to different first change ratios, wherein the particle estimator is configured to estimate a type of floating particles, corresponding to the relative change ratio, in the relative change ratio table, wherein the smoke density estimator is configured to estimate a smoke density, corresponding to the first change ratio, in the density table if the type of floating particles is smoke.

10. A fire alarm system as claimed in claim 9, wherein the sound source comprises a single sound source, wherein the controller is configured to drive the sound source so as to send the sound waves, having the first and second frequencies differing from each other, from the sound source sequentially, wherein the calculation means synchronizes the controller and is configured to calculate pressure ratios, in relation to the sound waves having the first and second frequencies, from the sound wave detector, respectively.

11. A fire alarm system as claimed in claim 5, wherein each of the first and second reflectors has a reflection surface formed into concave with respect to the wave-generating and wave-receiving elements located so as to face the first and second reflectors, respectively, wherein the reflectors is configured to let a sound wave collect in the wave-generating or wave-receiving elements, wherein the wave-generating and wave-receiving elements are located at exposed parts of the reflection surfaces of the first and second reflectors, respectively.

12. A fire alarm system as claimed in claim 5, wherein the first and second reflectors are located between a pair of nonproliferation plates, wherein at both ends in height directions of the first and second reflectors, the monitoring space is occluded with the nonproliferation plates wherein the wave-generating element is located at an intermediate part in a length direction of the first reflector, wherein at the intermediate part of the first reflector, a generation face of the wave-generating element is configured to cover the whole of a height direction of the first reflector.

* * * * *